(12) United States Patent
Kwon et al.

(10) Patent No.: US 11,696,904 B2
(45) Date of Patent: Jul. 11, 2023

(54) PRODRUG FOR THERAPEUTIC APPLICATIONS

(71) Applicant: The Regents of the University of California, Oakland, CA (US)

(72) Inventors: Young Jik Kwon, Irvine, CA (US); Jessica Kemp, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 138 days.

(21) Appl. No.: 17/145,306

(22) Filed: Jan. 9, 2021

(65) Prior Publication Data

US 2021/0212966 A1 Jul. 15, 2021

Related U.S. Application Data

(60) Provisional application No. 62/959,860, filed on Jan. 10, 2020.

(51) Int. Cl.
| | | |
|---|---|---|
| *A61K 31/137* | (2006.01) | |
| *A61P 35/00* | (2006.01) | |
| *A61K 45/06* | (2006.01) | |

(52) U.S. Cl.
CPC ............ *A61K 31/137* (2013.01); *A61K 45/06* (2013.01); *A61P 35/00* (2018.01)

(58) Field of Classification Search
CPC C07D 319/08; C07D 221/02; A61K 31/4427; A61K 31/4433; A61P 35/00
See application file for complete search history.

(56) References Cited

FOREIGN PATENT DOCUMENTS

WO WO-2005014603 A1 * 2/2005 .......... C07F 9/657118
WO WO-2013185740 A1 * 12/2013 ........... C07C 213/08

OTHER PUBLICATIONS

Masoudipour (Drug Discovery and Industrial Pharmacy vol. 44 pp. 99-108, published Oct. 17, 2017). (Year: 2017).*
Allen, T.M., "Ligand-targeted therapeutics in anticancer therapy." Nature Reviews Cancer 2(10):750-763 (2002).
Arroyo-Crespo et al., "Tumor microenvironment-targeted poly-L-glutamic acid-based combination conjugate for enhanced triple negative breast cancer treatment." Biomaterials 186:8-21 (2018).
Baer et al., "Characterization of the effects of immunomodulatory drug fingolimod (FTY720) on human T cell receptor signaling pathways." Scientific Reports 8 (1):10910 (2018).
Baker et al., "Epigenetic changes to the MDR1 locus in response to chemotherapeutic drugs." Oncogene 24:8061 (2005).
Barthelemy et al., "FTY720-induced endocytosis of yeast and human amino acid transporters is preceded by reduction of their inherent activity and TORC1 inhibition." Scientific reports 7(1):13816-13816 (2017).
Brannon-Peppas et al., "anoparticle and targeted systems for cancer therapy." Advanced drug delivery reviews 64:206-212 (2012).
Brown et al., "Exploiting tumour hypoxia in cancer treatment." Nature Reviews Cancer 4(6):437 (2004).
Budman et al., Dose and dose intensity as determinants of outcome in the adjuvant treatment of breast cancer. JNCI: Journal of the National Cancer Institute 90(16):1205-1211 (1998).
Camm et al., "Cardiac and vascular effects of fingolimod: mechanistic basis and clinical implications." American heart journal 168(5):632-644 (2014).
Cavallaro et al., "Synthesis, physico-chemical and biological characterization of a paclitaxel macromolecular prodrug." 58:151-9 (2004).
Chen et al., "Charge-conversional and reduction-sensitive poly(vinyl alcohol) nanogels for enhanced cell uptake and efficient intracellular doxorubicin release" Journal of Controlled Release 205:15-24 (2015).
Chen et al., "Azacyclic FTY720 Analogues That Limit Nutrient Transporter Expression but Lack S1P Receptor Activity and Negative Chronotropic Effects Offer a Novel and Effective Strategy to Kill Cancer Cells in Vivo." ACS chemical biology 11(2):409-414 (2016).
Chytil et al., "HPMA Copolymer-Drug Conjugates with Controlled Tumor-Specific Drug Release." Macromolecular bioscience 18(1):1700209 (2018).
Cohen et al., "Mechanisms of fingolimod's efficacy and adverse effects in multiple sclerosis." Annals of neurology 69(5):759-777 (2011).
Dang, C. V., "Links between metabolism and cancer." Genes Dev 26(9):877-890 (2012).
De Palma et al., "The NMR-based characterization of the FTY720-SET complex reveals an alternative mechanism for the attenuation of the inhibitory SET-PP2A interaction." The FASEB Journal 33(6):7647-7666 (2019).
Deslongchamps et al., "The relative rate of hydrolysis of a series of acyclic and six-membered cyclic acetals, ketals, orthoesters, and orthocarbonates." Tetrahedron 56(22):3533-3537 (2000).
Deutsch et al., "Investigations on heterogeneously catalysed condensations of glycerol to cyclic acetals." Journal of Catalysis 245(2):428-435 (2007).
Dimasi et al., "The price of innovation: new estimates of drug development costs." Journal of Health Economics 22(2):151-185 (2003).
Durso et al., "Acceleration of leukocytes' epigenetic age as an early tumor and sex-specific marker of breast and colorectal cancer." Oncotarget 8(14):23237-23245 (2017).
Edinger et al., "Akt maintains cell size and survival by increasing mTOR-dependent nutrient uptake". Mol Biol Cell 13(7):2276-2288. (2002).

(Continued)

*Primary Examiner* — Theodore R. Howell
*Assistant Examiner* — George W Kosturko
(74) *Attorney, Agent, or Firm* — Gavrilovich, Dodd & Lindsey LLP

(57) ABSTRACT

The disclosure provides for prodrugs of Fingolimod that were designed to specifically prevent phosphorylation during circulation, hence avoiding bradycardia and lymphopenia. The disclosure further provides for the use of the prodrugs in the treatment of cancer and multiple sclerosis in subjects in need of treatment thereof.

16 Claims, 13 Drawing Sheets

(56) References Cited

OTHER PUBLICATIONS

Freeman et al., "Fully synthetic macromolecular prodrug chemotherapeutics with EGFR targeting and controlled camptothecin release kinetics." Polymer Chemistry 9(42):5224-5233 (2018).
Feinberg et al., "he key role of epigenetics in human disease prevention and mitigation." New England Journal of Medicine 378(14):1323-1334 (2018).
Freije et al., "Review of Drugs Approved via the 505(b)(2) Pathway: Uncovering Drug Development Trends and Regulatory Requirements." Therapeutic Innovation & Regulatory Science 54(1):128-138 (Jan. 2020).
Jin et al., "Metabolic catastrophe as a means to cancer cell death." Journal of Cell Science 120(3):379 (2007).
Kemp et al, ""Combo" nanomedicine: co-delivery of multi-modal therapeutics for efficient, targeted, and safe cancer therapy." Advanced drug delivery reviews 98:3-18 (2016).
Kemp et al, "Biocompatible Chemotherapy for Leukemia by Acid-Cleavable, PEGylated FTY720." Bioconjugate Chem 31:673-684 (2020).
Kerbel et al., "Clinical translation of angiogenesis inhibitors." Nature Reviews Cancer 2(10):727 (2002).
Kihara et al., "Production and release of sphingosine 1-phosphate and the phosphorylated form of the immunomodulator FTY720." Biochimica et Biophysica Acta (BBA)—Molecular and Cell Biology of Lipids 1781(9):496-502 (2008).
Kim et al., "Targeting cancer metabolism by simultaneously disrupting parallel nutrient access pathways." The Journal of clinical investigation 126(11):4088-4102 (2016).
Kirby et al., "Intramolecular proton-transfer catalysis of nucleophilic catalysis of acetal hydrolysis. The hydrolysis of 8-dimethylamino-1-methoxymethoxynaphthalene." Journal of the Chemical Society, Perkin Transactions 2 7:907-912 (1989).
Koyrakh et al., "The Heart Rate Decrease Caused by Acute FTY720 Administration Is Mediated by the G Protein-Gated Potassium Channel I." Am J Transplant 5(3):529-36 (2005).
Kwon et al.,"Gold Cluster-Labeled Thermosensitive Liposomes Enhance Triggered Drug Release in the Tumor Microenvironment by a Photothermal Effect." Journal of Controlled Release 216:132-139 (2015).
Lee et al., "Polymeric micelle for tumor pH and folate-mediated targeting." Journal of Controlled Release 91(1):103-113 (2003).
Liu et al., "Comb-shaped, temperature-tunable and water-soluble porphyrin-based thermoresponsive copolymer for enhanced photodynamic therapy." Materials Science and Engineering: C 82:155-162 (2018).
Mccracken et al., "Phosphorylation of a constrained azacyclic FTY720 analog enhances anti-leukemic activity without inducing S1P receptor activation." Leukemia 31:669-677 (2016).
Murthy et al., "A Novel Strategy for Encapsulation and Release of Proteins: Hydrogels and Microgels with Acid-Labile Acetal Cross-Linkers." 124:12398-9 (2002).
Neviani et al., "FTY720, a new alternative for treating blast crisis chronic myelogenous leukemia and Philadelphia chromosome-positive acute lymphocytic leukemia." The Journal of Clinical Investigation 117(9):2408-2421 (2007).
Oaks et al., "Antagonistic activities of the immunomodulator and PP2A-activating drug FTY720 (Fingolimod, Gilenya) in Jak2-driven hematologic malignancies." Blood 122(11):1923-1934 (2013).
Pacardo et al., "Programmable nanomedicine: synergistic and sequential drug delivery systems." Nanoscale 7(8):3381-3391 (2015).
Park et al., "Addressing drug resistance in cancer with macromolecular chemotherapeutic agents." Journal of the American Chemical Society 140(12):4244-4252 (2018).
Peer et al., "Nanocarriers as an emerging platform for cancer therapy." Nature Nanotechnology 2:751-760 (2007).
Priest et al., "A syndrome of thrombosis and hemorrhage complicating L-asparaginase therapy for childhood acute lymphoblastic leukemia." The Journal of pediatrics 100 (6):984-989 (1982).

QilN et al., "Mechanistic understanding the bioeffects of ultrasound-driven microbubbles to enhance macromolecule delivery." Journal of controlled release 272:169-181 (2018).
Rabinowitz et al., "Autophagy and metabolism." Science 330(6009):1344-1348 (2010).
Rautio et al., "The expanding role of prodrugs in contemporary drug design and development." Nature Reviews Drug Discovery 17:559 (2018).
Rios et al., "pH valve based on hydrophobicity switching." Chemistry of Materials 23(16):3601-3605 (2011).
Romero Rosales et al., "Sphingolipid-based drugs selectively kill cancer cells by down-regulating nutrient transporter proteins." The Biochemical journal 439(2):299-311 (2011).
Sakai et al., "Effects of doxorubicin on sperm DNA methylation in mouse models of testicular toxicity." Biochemical and biophysical research communications 498(3):674-679 (2018).
Sanna et al., "Sphingosine 1-phosphate (S1P) receptor subtypes S1P1 and S1P3, respectively, regulate lymphocyte recirculation and heart rate." Journal of Biological Chemistry 279(14):13839-13848 (2004).
Sawyers, C., "Targeted cancer therapy." Nature 432(7015):294-297 (2004).
Selwan et al., "Attacking the supply wagons to starve cancer cells to death." FEBS Lett 590(7):885-907 (2016).
Shin et al., "Dysregulation of epidermal growth factor receptor expression in premalignant lesions during head and neck tumorigenesis." Cancer research 54(12):3153-3159 (1994).
Shishavan et al., "Differential Effects of Long Term FTY720 Treatment on Endothelial versus Smooth Muscle Cell Signaling to S1P in Rat Mesenteric Arteries." PloS one 11(9):e0162029 (2016).
Smith et al., "The pH-Rate Profile for the Hydrolysis of a Peptide Bond." Journal of the American Chemical Society 120(35):8910-8913 (1998).
Song et al., "DNA hydrogel delivery vehicle for light-triggered and synergistic cancer therapy." 7:9433-9437 (2015).
Soyez et al., "The crucial role of spacer groups in macromolecular prodrug design." Advanced Drug Delivery Reviews 21(2):81-106 (1996).
Stafmann et al., "P2A activation alone and in combination with cisplatin decreases cell growth and tumor formation in human HuH6 hepatoblastoma cells." PloS one 14(4):e0214469 (2019).
Tannock et al., "Acid pH in tumors and its potential for therapeutic exploitation." Cancer Research 49(16), 4373-4384 (1989).
Thambi et al., "15-Stimuli-responsive polymersomes for cancer therapy." Stimuli Responsive Polymeric Nanocarriers for Drug Delivery Applications 413-438 (2019).
Tomita et al., "Amino acid metabolomics using LC-MS/MS: Assessment of cancer-cell resistance in a simulated tumor microenvironment." Analytical Sciences 32(8),:893-900 (2016).
Tretyakova et al., "Epigenetics in Toxicology." Chemical Research in Toxicology 32(5):793-793 (2019).
Vander Heiden et al., "Targeting cancer metabolism: a therapeutic window opens." Nature Reviews Drug Discovery 10:671 (2011).
Vanneman et al., "Combining immunotherapy and targeted therapies in cancer treatment." Nature Reviews Cancer 12(4):237-251 (2012).
Vasir et al., "Targeted Drug Delivery in Cancer Therapy." Technology in Cancer Research & Treatment 4(4):363-374 (2005).
Venkataraman et al., "Extracellular export of sphingosine kinase-1a contributes to the vascular S1P gradient." Biochemical Journal 397(3):461-471(2006).
Verhoef et al.,"Questioning the Use of PEGylation for Drug Delivery." Drug Delivery and Translational Research 3(6), 499-503. (2013).
Widakowich et al., "Side effects of approved molecular targeted therapies in solid cancers." The Oncologist 12(12):1443-1455 (2007).
Yan et al., "Lipase-catalyzed solid-phase synthesis of sugar fatty acid esters: removal of byproducts by azeotropic distillation." Enzyme and microbial technology 25(8-9):725-728 (1999).
Yatomi et al., "Sphingosine-1-phosphate: a platelet-activating sphingolipid released from agonist-stimulated human platelets." Blood 86(1):193-202 (1995).

(56) References Cited

OTHER PUBLICATIONS

You et al., "A Drug-Delivery Vehicle Combining the Targeting and Thermal Ablation of HER2+ Breast-Cancer Cells with Triggered Drug Release." 52(15):4141-4146 (2013).

Zhang et al., "Starved and asphyxiated: how can CD8+ T cells within a tumor microenvironment prevent tumor progression." Frontiers in Immunology 7(32):1-7 (2016).

Zhang et al., "Binding of HSA to Macromolecular p HPMA Based Nanoparticles for Drug Delivery: An Investigation Using Fluorescence Methods." Langmuir 34(27):7998-8006 (2018).

Zhou et al., "Combination Drug Release of Smart Cyclodextrin-Gated Mesoporous Silica Nanovehicles." Chemical Communications 51:7203-7206 (2015).

\* cited by examiner

A

B

FTY720

PRODRUG FOR THERAPEUTIC APPLICATIONS

CROSS REFERENCE TO RELATED APPLICATIONS

This application claims priority under 35 U.S.C. § 119 from Provisional Application Ser. No. 62/959,860 filed Jan. 10, 2020, the disclosure of which is incorporated herein by reference.

TECHNICAL FIELD

The disclosure provides for a prodrug of fingolimod, and uses thereof including for treating multiple sclerosis and cancer.

BACKGROUND

Targeting the inability of cancerous cells to adapt to metabolic stress is a promising alternative to conventional cancer chemotherapy. Fingolimod (FTY720), an FDA-approved drug for the treatment of multiple sclerosis, has recently been shown to inhibit cancer progression through the down-regulation of essential nutrient transport proteins, selectively starving cancer cells to death. However, the clinical use of fingolimod for cancer therapy is prohibited due to its capability of inducing immunosuppression (lymphopenia) and bradycardia when phosphorylated upon administration.

SUMMARY

The disclosure provides for prodrugs of fingolimod that were designed to specifically prevent phosphorylation during circulation, hence avoiding bradycardia and lymphopenia. In a particular embodiment, a prodrug of the disclosure was synthesized by capping fingolimod hydroxyl groups with polyethylene glycol (PEG) via an acid-cleavable ketal linkage. Improved aqueous solubility was also accomplished by PEGylation. The prodrugs described herein were converted to fully potent fingolimod upon cellular uptake and induced metabolic stress in cancer cells. The prodrugs of the disclosure demonstrated effective fingolimod release in a mildly acidic endosomal pH and substantially down-regulated cell-surface nutrient transporter proteins in leukemia cells. Importantly, the prodrugs of the disclosure demonstrated nearly identical efficacy to fingolimod in an animal model of BCR-Abl-driven leukemia without inducing bradycardia or lymphopenia in vivo, highlighting the prodrugs potential clinical value. The prodrug formulation of fingolimod demonstrates the utility of precisely engineering a drug to avoid undesirable effects by tackling specific molecular mechanisms as well as a financially favorable alternative to new drug development. A multitude of existing cancer therapeutics may be explored for prodrug formulation to avoid specific side effects and preserve or enhance therapeutic efficacy.

In a particular embodiment, the disclosure provides for a prodrug of fingolimod comprising a stimuli-responsive linker that is cleaved when exposed to environmental stimuli, external stimuli, or specific biological processes, to release the active drug fingolimod. In a further embodiment, the environmental stimuli are selected from acidic environment, basic environment, and reducing environment. In another embodiment, the external stimuli are selected from heat, ultrasound, photo-irradiation, an electrochemical field, and a magnetic field. In yet another embodiment, the biological processes are selected from enzymatic cleavage and ion chelation. In a further embodiment, the enzymatic cleavage is by esterases, or phosphatases. In a certain embodiment, the prodrug comprises the structure of Formula I(a) or Formula I(b):

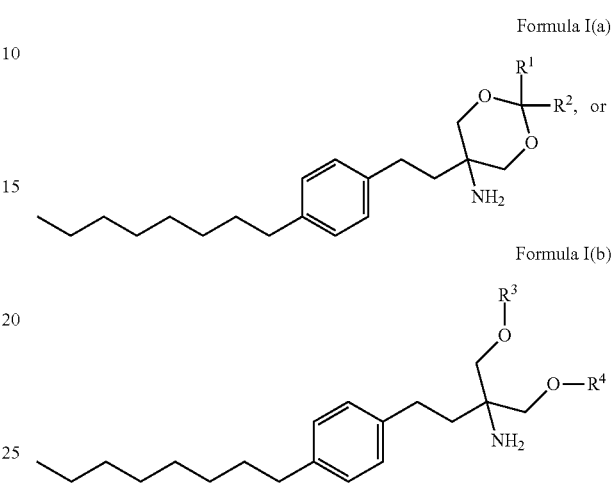

or a pharmaceutically acceptable salt or solvate thereof, wherein, $R^1$ is selected from H, D,

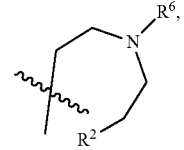

optionally substituted $(C_1\text{-}C_{30})$alkyl, optionally substituted $(C_1\text{-}C_{30})$heteroalkyl, optionally substituted $(C_1\text{-}C_{30})$alkenyl, optionally substituted $(C_1\text{-}C_{30})$heteroalkenyl, optionally substituted $(C_1\text{-}C_{30})$alkynyl, optionally substituted $(C_1\text{-}C_{30})$heteroalkynyl, optionally substituted aryl, optionally substituted $(C_3\text{-}C_{12})$cycloalkyl, optionally substituted $(C_4\text{-}C_{12})$cycloalkenyl, optionally substituted heterocycle, optionally substituted heteroaryl, optionally substituted mixed ring system, optionally substituted $(C_2\text{-}C_{30})$-alkoxy, optionally substituted $(C_2\text{-}C_{30})$-ester, polyethyleneimine, poly(glycolic acid), a poly(lactic acid), poly(glycolic-co-lactic acid), chitosan, poly(methacrylic acid), poly(acrylic acid), polycaprolactone, poly(ethylene/vinyl acetate), poly(vinyl acetate), poly(vinyl methyl ether), poly(vinyl alcohol), poly (N-isopropylacrylamide), —OH, a lipid, a saccharide, a polysaccharide, a nucleic acid, an amino acid, a peptide, a peptoid, a fatty acid, ethylene glycol, and polyethylene glycol; $R^2$ is selected from

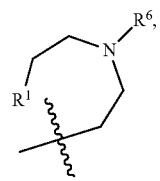

optionally substituted ($C_1$-$C_{30}$)alkyl, optionally substituted ($C_1$-$C_{30}$)heteroalkyl, optionally substituted ($C_1$-$C_{30}$) alkenyl, optionally substituted ($C_1$-$C_{30}$) heteroalkenyl, optionally substituted ($C_1$-$C_{30}$)alkynyl, optionally substituted ($C_1$-$C_{30}$)heteroalkynyl, optionally substituted aryl, optionally substituted ($C_3$-$C_{12}$)cycloalkyl, optionally substituted ($C_4$-$C_{12}$)cycloalkenyl, optionally substituted heterocycle, optionally substituted heteroaryl, optionally substituted mixed ring system, optionally substituted ($C_2$-$C_{30}$)-alkoxy, optionally substituted ($C_2$-$C_{30}$)-ester, polyethyleneimine, poly(glycolic acid), a poly(lactic acid), poly(glycolic-co-lactic acid), chitosan, poly(methacrylic acid), poly(acrylic acid), polycaprolactone, poly(ethylene/vinyl acetate), poly(vinyl acetate), poly(vinyl methyl ether), poly(vinyl alcohol), poly (N-isopropylacrylamide), —OH, a lipid, a saccharide, a polysaccharide, a nucleic acid, an amino acid, a peptide, a peptoid, a fatty acid, ethylene glycol, and polyethylene glycol; $R^3$ and $R^4$ are independently selected from

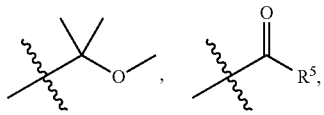

optionally substituted ($C_1$-$C_{30}$)alkyl, optionally substituted ($C_1$-$C_{30}$)heteroalkyl, optionally substituted ($C_1$-$C_{30}$)alkenyl, optionally substituted ($C_1$-$C_{30}$)heteroalkenyl, optionally substituted ($C_1$-$C_{30}$)alkynyl, optionally substituted ($C_1$-$C_{30}$) heteroalkynyl, optionally substituted aryl, optionally substituted ($C_3$-$C_{12}$)cycloalkyl, optionally substituted ($C_4$-$C_{12}$)cycloalkenyl, optionally substituted heterocycle, optionally substituted heteroaryl, optionally substituted mixed ring system, optionally substituted ($C_2$-$C_{30}$)-alkoxy, optionally substituted ($C_2$-$C_{30}$)-ester, polyethyleneimine, poly(glycolic acid), a poly(lactic acid), poly(glycolic-co-lactic acid), chitosan, poly(methacrylic acid), poly(acrylic acid), polycaprolactone, poly(ethylene/vinyl acetate), poly(vinyl acetate), poly(vinyl methyl ether), poly(vinyl alcohol), poly (N-isopropylacrylamide), a lipid, a saccharide, a polysaccharide, a nucleic acid, an amino acid, a peptide, a peptoid, a fatty acid, ethylene glycol, and polyethylene glycol; and $R^5$ is selected from optionally substituted ($C_1$-$C_{30}$)alkyl, optionally substituted ($C_1$-$C_{30}$)heteroalkyl, optionally substituted ($C_1$-$C_{30}$) alkenyl, optionally substituted ($C_1$-$C_{30}$)heteroalkenyl, optionally substituted ($C_1$-$C_{30}$)alkynyl, optionally substituted ($C_1$-$C_{30}$)heteroalkynyl, optionally substituted aryl, optionally substituted ($C_3$-$C_{12}$)cycloalkyl, optionally substituted ($C_4$-$C_{12}$)cycloalkenyl, optionally substituted heterocycle, optionally substituted heteroaryl, optionally substituted mixed ring system, optionally substituted ($C_2$-$C_{30}$)-alkoxy, optionally substituted ($C_2$-$C_{30}$)-ester, polyethyleneimine, poly(glycolic acid), a poly(lactic acid), poly(glycolic-co-lactic acid), chitosan, poly(methacrylic acid), poly(acrylic acid), polycaprolactone, poly(ethylene/vinyl acetate), poly(vinyl acetate), poly(vinyl methyl ether), poly(vinyl alcohol), poly (N-isopropylacrylamide), —OH, a lipid, a saccharide, a polysaccharide, a nucleic acid, an amino acid, a peptide, a peptoid, a fatty acid, ethylene glycol, and polyethylene glycol; $R^6$ is selected from H, D,

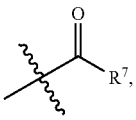

optionally substituted ($C_1$-$C_{30}$)alkyl, optionally substituted ($C_1$-$C_{30}$)heteroalkyl, optionally substituted ($C_1$-$C_{30}$) alkenyl, optionally substituted ($C_1$-$C_{30}$) heteroalkenyl, optionally substituted ($C_1$-$C_{30}$)alkynyl, optionally substituted ($C_1$-$C_{30}$)heteroalkynyl, optionally substituted aryl, optionally substituted ($C_3$-$C_{12}$)cycloalkyl, optionally substituted ($C_4$-$C_{12}$)cycloalkenyl, optionally substituted heterocycle, optionally substituted heteroaryl, optionally substituted mixed ring system, optionally substituted ($C_2$-$C_{30}$)-alkoxy, optionally substituted ($C_2$-$C_{30}$)-ester, polyethyleneimine, poly(glycolic acid), a poly(lactic acid), poly(glycolic-co-lactic acid), chitosan, poly(methacrylic acid), poly(acrylic acid), polycaprolactone, poly(ethylene/vinyl acetate), poly(vinyl acetate), poly(vinyl methyl ether), poly(vinyl alcohol), poly (N-isopropylacrylamide), —OH, a lipid, a saccharide, a polysaccharide, a nucleic acid, an amino acid, a peptide, a peptoid, a fatty acid, ethylene glycol, and polyethylene glycol; and $R^7$ is selected from optionally substituted ($C_1$-$C_{30}$)alkyl, optionally substituted ($C_1$-$C_{30}$)heteroalkyl, optionally substituted ($C_1$-$C_{30}$)alkenyl, optionally substituted ($C_1$-$C_{30}$)heteroalkenyl, optionally substituted ($C_1$-$C_{30}$)alkynyl, optionally substituted ($C_1$-$C_{30}$)heteroalkynyl, optionally substituted aryl, optionally substituted ($C_3$-$C_{12}$)cycloalkyl, optionally substituted ($C_4$-$C_{12}$)cycloalkenyl, optionally substituted heterocycle, optionally substituted heteroaryl, optionally substituted mixed ring system, optionally substituted ($C_2$-$C_{30}$)-alkoxy, optionally substituted ($C_2$-$C_{30}$)-ester, polyethyleneimine, poly(glycolic acid), a poly(lactic acid), poly(glycolic-co-lactic acid), chitosan, poly(methacrylic acid), poly(acrylic acid), polycaprolactone, poly(ethylene/vinyl acetate), poly(vinyl acetate), poly(vinyl methyl ether), poly(vinyl alcohol), poly (N-isopropylacrylamide), —OH, a lipid, a saccharide, a polysaccharide, a nucleic acid, an amino acid, a peptide, a peptoid, a fatty acid, ethylene glycol, and polyethylene glycol. In another embodiment, the prodrug comprises the structure of Formula II:

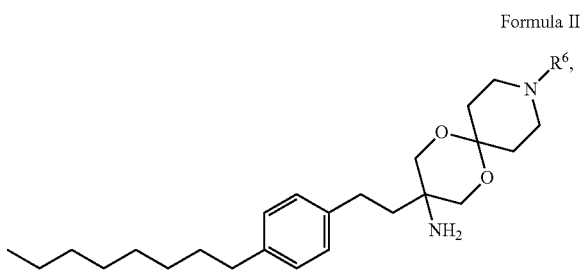

Formula II or a pharmaceutically acceptable salt or solvate thereof, wherein, $R^6$ is selected from H, D, cycloalkenyl, optionally substituted heterocycle, optionally substituted heteroaryl, optionally substituted mixed ring system, optionally substituted ($C_2$-$C_{30}$)-alkoxy, optionally substituted ($C_2$-$C_{30}$)-ester, polyethyleneimine, poly(glycolic acid), a poly(lactic acid), poly(glycolic-co-lactic acid), chitosan, poly(methacrylic acid), poly(acrylic acid), polycaprolactone, poly(ethylene/vinyl acetate), poly(vinyl acetate), poly(vinyl methyl ether), poly(vinyl alcohol), poly (N-isopropylacrylamide), —OH, a lipid, a saccharide, a polysaccharide, a nucleic acid, an amino acid, a peptide, a peptoid, a fatty acid, ethylene glycol, and polyethylene glycol; and $R^7$ is selected from an optionally substituted ($C_1$-$C_{30}$)alkyl, optionally substituted ($C_1$-$C_{30}$)heteroalkyl, optionally substituted ($C_1$-$C_{30}$) alkenyl, optionally substituted ($C_1$-$C_{30}$) heteroalkenyl, optionally substituted ($C_1$-$C_{30}$)alkynyl, optionally substituted ($C_1$-$C_{30}$)heteroalkynyl, optionally substituted aryl, optionally substituted ($C_3$-$C_{12}$)cycloalkyl, optionally substituted ($C_4$-$C_{12}$)cycloalkenyl, optionally substituted heterocycle, optionally substituted heteroaryl, optionally substituted mixed ring system, optionally substituted ($C_2$-$C_{30}$)-alkoxy, optionally substituted ($C_2$-$C_{30}$)-ester, polyethyleneimine, poly(glycolic acid), a poly(lactic acid), poly(glycolic-co-lactic acid), chitosan, poly(methacrylic acid), poly(acrylic acid), polycaprolactone, poly(ethylene/vinyl acetate), poly(vinyl acetate), poly(vinyl methyl ether), poly(vinyl alcohol), poly (N-isopropylacrylamide), —OH, a lipid, a saccharide, a polysaccharide, a nucleic acid, an amino acid, a peptide, a peptoid, a fatty acid, ethylene glycol, and polyethylene glycol. In yet another embodiment, the prodrug is a pharmaceutically acceptable salt form of the prodrug having the structure of Formula II(a):

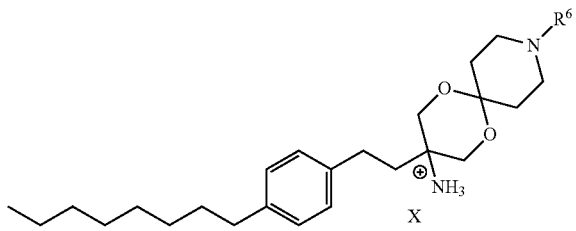

Formula II (a)

wherein, $R^6$ is selected from H, D,

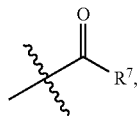

optionally substituted ($C_1$-$C_{30}$) alkyl, optionally substituted ($C_1$-$C_{30}$) heteroalkyl, optionally substituted ($C_1$-$C_{30}$)alkenyl, optionally substituted ($C_1$-$C_{30}$)heteroalkenyl, optionally substituted ($C_1$-$C_{30}$)alkynyl, optionally substituted ($C_1$-$C_{30}$)heteroalkynyl, optionally substituted aryl, optionally substituted ($C_3$-$C_{12}$)cycloalkyl, optionally substituted ($C_4$-$C_{12}$)cycloalkenyl, optionally substituted heterocycle, optionally substituted heteroaryl, optionally substituted mixed ring system, optionally substituted ($C_2$-$C_{30}$)-alkoxy, optionally substituted ($C_2$-$C_{30}$)-ester, polyethyleneimine, poly(glycolic acid), a poly(lactic acid), poly(glycolic-co-lactic acid), chitosan, poly(methacrylic acid), poly(acrylic acid), polycaprolactone, poly(ethylene/vinyl acetate), poly(vinyl acetate), poly(vinyl methyl ether), poly(vinyl alcohol), poly (N-isopropylacrylamide), —OH, a lipid, a saccharide, a polysaccharide, a nucleic acid, an amino acid, a peptide, a peptoid, a fatty acid, ethylene glycol, and polyethylene glycol; $R^7$ is selected from optionally substituted ($C_1$-$C_{30}$)alkyl, optionally substituted ($C_1$-$C_{30}$)heteroalkyl, optionally substituted ($C_1$-$C_{30}$)alkenyl, optionally substituted ($C_1$-$C_{30}$)heteroalkenyl, optionally substituted ($C_1$-$C_{30}$) alkynyl, optionally substituted ($C_1$-$C_{30}$)heteroalkynyl, optionally substituted aryl, optionally substituted ($C_3$-$C_{12}$) cycloalkyl, optionally substituted ($C_4$-$C_{12}$)cycloalkenyl, optionally substituted heterocycle, optionally substituted heteroaryl, optionally substituted mixed ring system, optionally substituted ($C_2$-$C_{30}$)-alkoxy, optionally substituted ($C_2$-$C_{30}$)-ester, polyethyleneimine, poly(glycolic acid), a poly (lactic acid), poly(glycolic-co-lactic acid), chitosan, poly (methacrylic acid), poly(acrylic acid), polycaprolactone, poly(ethylene/vinyl acetate), poly(vinyl acetate), poly(vinyl methyl ether), poly(vinyl alcohol), poly (N-isopropylacrylamide), —OH, a lipid, a saccharide, a polysaccharide, a nucleic acid, an amino acid, a peptide, a peptoid, a fatty acid, ethylene glycol, and polyethylene glycol; and X is a counterion selected from the group consisting of acetate, aspartate, benzenesulfonate, benzoate, besylate, bicarbonate, bitartrate, bromide, camsylate, carbonate, chloride, citrate, decanoate, edetate, esylate, fumarate, gluceptate, gluconate, glutamate, glycolate, hexanoate, hydroxynaphthoate, iodide, isethionate, lactate, lactobionate, malate, maleate, mandelate, mesylate, methylsulfate, mucate, napsylate, nitrate, octanoate, oleate, pamoate, pantothenate, phosphate, polygalacturonate, propionate, salicylate, stearate, succinate, sulfate, tartrate, teoclate and tosylate. In another embodiment, the prodrug comprises the structure of Formula III:

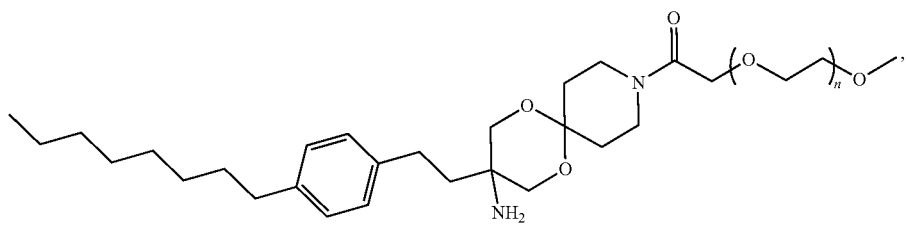

Formula III or a pharmaceutically acceptable salt or solvate thereof, wherein, n is an integer selected from 1 to 400,000. In yet another embodiment, the prodrug is a pharmaceutically acceptable salt form of the prodrug having the structure of Formula III(a):

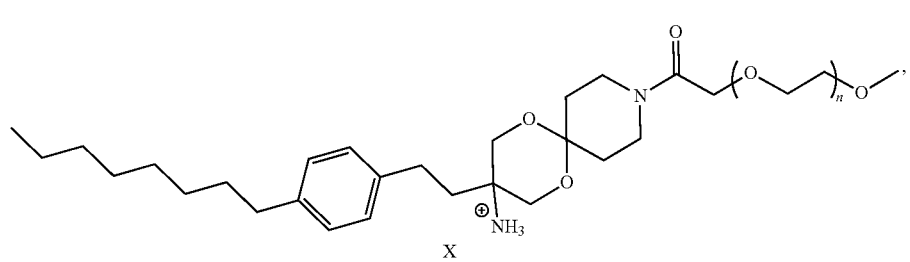

Formula III (a)

wherein, n is an integer selected from 1 to 400,000; and X is a counterion selected from the group consisting of acetate, aspartate, benzenesulfonate, benzoate, besylate, bicarbonate, bitartrate, bromide, camsylate, carbonate, chloride, citrate, decanoate, edetate, esylate, fumarate, gluceptate, gluconate, glutamate, glycolate, hexanoate, hydroxynaphthoate, iodide, isethionate, lactate, lactobionate, malate, maleate, mandelate, mesylate, methylsulfate, mucate, napsylate, nitrate, octanoate, oleate, pamoate, pantothenate, phosphate, polygalacturonate, propionate, salicylate, stearate, succinate, sulfate, tartrate, teoclate and tosylate. In yet a further embodiment, the prodrug is fully converted to fingolimod when exposed to a pH from 4.5 to 6.5.

The disclosure also provides for a pharmaceutical composition comprising a prodrug of the disclosure and a pharmaceutically acceptable carrier, diluent, and/or excipient. In another embodiment, the pharmaceutical composition is formulated for oral or parenteral administration. In yet another embodiment, the pharmaceutical composition is in the form of enterically coated tablets, capsules, or pills for oral delivery. In a further embodiment, the pharmaceutical composition is in the form or enterically coated hard gelatin capsule which further comprises mannitol, magnesium stearate, titanium dioxide, and/or yellow iron oxide.

The disclosure further provides for a method of treating a subject with a cancer, comprising: administering a therapeutically effective amount of a prodrug disclosed herein, or a pharmaceutical composition disclosed herein to the subject in need of treatment thereof. In another embodiment, the cancer is selected from the group consisting of adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, urinary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodeimal tumors, visual pathway and hypothalamic glioma, breast cancer, including triple negative breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, soft tissue sarcoma, uterine cancer, uterine sarcoma, skin cancer (non-melanoma), skin cancer (melanoma), papillomas, actinic keratosis and keratoacanthomas, merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor. In a further embodiment, the cancer is selected from the group consisting of a chronic myelogenous leukemia (CML), acute lymphoblastic leukemia (ALL), non-small cell lung cancer (NSCLC), breast cancer, melanoma, colorectal cancer, and ovarian cancer. In a certain embodiment, the prodrug is administered at a dose from 100 mg/kg to 1000 mg/kg. In another embodiment, the prodrug is administered at a dose from 150 mg/kg to 500 mg/kg. In another embodiment, the method further comprises administering, sequentially or concurrently, one or more anticancer therapeutic agents selected from the group consisting of angiogenesis inhibitors, tyrosine kinase inhibitors, PARP inhibitors, alkylating agents, vinca alkaloids, anthracyclines, antitumor antibiotics, antimetabolites, topoisomerase inhibitors, aromatase inhibitors, mTor inhibitors, retinoids, and HDAC inhibitors.

The disclosure provides a method of treating a subject with multiple sclerosis, comprising: administering an effective amount of the prodrug of any one of claims 1 to 10, or the pharmaceutical composition of any one of claims 11 to 15 to the subject in need of treatment thereof. In a further embodiment, the method further comprises administering, sequentially or concurrently, one or more multiple sclerosis treatments selected from the group consisting of beta interferons, glatiramer acetate, dimethyl fumarate, teriflunomide, siponimod, ocrelizumab, natalizumab, alemtuzumab, and mitoxantrone.

In a particular embodiment, the disclosure provides a prodrug of fingolimod comprising an acid-labile linkage that when exposed to an environment that has a pH<7.0 releases the parent drug fingolimod. In a further embodiment, the acid-labile linkage comprises a group selected from an acetal, a ketal, a hydrazone, a cis-aconityl, and a carbamate. In yet a further embodiment, the acid-labile linkage comprises a ketal group. In another embodiment, the acid-labile linkage is PEGylated. In yet another embodiment, the prodrug does not release the parent drug when exposed to physiological pH of 7.4. In a certain embodiment, the parent drug is released from the prodrug when exposed to a pH from 4.2 to 6.7. In a further embodiment, the prodrug in comparison to the parent drug is not phosphorylated during circulation in vivo. In yet a further embodiment, the prodrug comprises the structure of Formula II:

Formula II

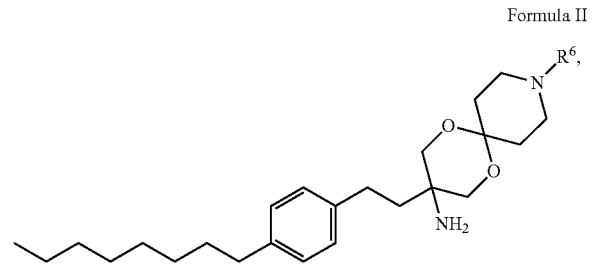

or a pharmaceutically acceptable salt or solvate thereof, wherein, $R^6$ is selected from H, D,

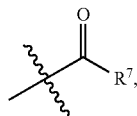

optionally substituted $(C_1-C_{30})$alkyl, optionally substituted $(C_1-C_{30})$heteroalkyl, optionally substituted $(C_1-C_{30})$alkenyl, optionally substituted $(C_1-C_{30})$heteroalkenyl, optionally substituted $(C_1-C_{30})$alkynyl, optionally substituted $(C_1-C_{30})$heteroalkynyl, optionally substituted aryl, optionally substituted $(C_3-C_{12})$cycloalkyl, optionally substituted $(C_4-C_{12})$cycloalkenyl, optionally substituted heterocycle, optionally substituted heteroaryl, optionally substituted mixed ring system, optionally substituted $(C_2-C_{30})$-alkoxy, optionally substituted $(C_2-C_{30})$-ester, polyethyleneimine, poly(glycolic acid), a poly(lactic acid), poly(glycolic-co-lactic acid), chitosan, poly(methacrylic acid), poly(acrylic acid), polycaprolactone, poly(ethylene/vinyl acetate), poly(vinyl acetate), poly(vinyl methyl ether), poly(vinyl alcohol), poly (N-isopropylacrylamide), —OH, a lipid, a saccharide, a polysaccharide, a nucleic acid, an amino acid, a peptide, a peptoid, a fatty acid, ethylene glycol, and polyethylene glycol; and $R^7$ is selected from an optionally substituted $(C_1-C_{30})$alkyl, optionally substituted $(C_1-C_{30})$heteroalkyl, optionally substituted $(C_1-C_{30})$ alkenyl, optionally substituted $(C_1-C_{30})$ heteroalkenyl, optionally substituted $(C_1-C_{30})$alkynyl, optionally substituted $(C_1-C_{30})$heteroalkynyl, optionally substituted aryl, optionally substituted $(C_3-C_{12})$cycloalkyl, optionally substituted $(C_4-C_{12})$cycloalkenyl, optionally substituted heterocycle, optionally substituted heteroaryl, optionally substituted mixed ring system, optionally substituted $(C_2-C_{30})$-alkoxy, optionally substituted $(C_2-C_{30})$-ester, polyethyleneimine, poly(glycolic acid), a poly(lactic acid), poly(glycolic-co-lactic acid), chitosan, poly(methacrylic acid), poly(acrylic acid), polycaprolactone, poly(ethylene/vinyl acetate), poly(vinyl acetate), poly(vinyl methyl ether), poly(vinyl alcohol), poly (N-isopropylacrylamide), —OH, a lipid, a saccharide, a polysaccharide, a nucleic acid, an amino acid, a peptide, a peptoid, a fatty acid, ethylene glycol, and polyethylene glycol. IN yet another embodiment, the prodrug is a pharmaceutically acceptable salt form of the prodrug having the structure of Formula II(a):

Formula II (a)

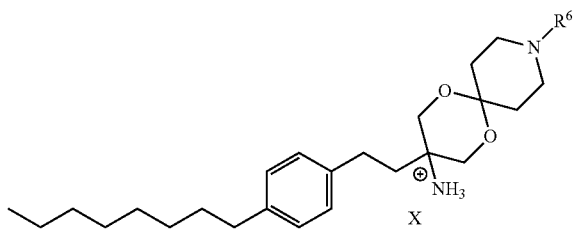

wherein, $R^6$ is selected from H, D,

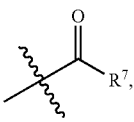

optionally substituted $(C_1-C_{30})$ alkyl, optionally substituted $(C_1-C_{30})$ heteroalkyl, optionally substituted $(C_1-C_{30})$alkenyl, optionally substituted $(C_1-C_{30})$heteroalkenyl, optionally substituted $(C_1-C_{30})$alkynyl, optionally substituted $(C_1-C_{30})$heteroalkynyl, optionally substituted aryl, optionally substituted $(C_3-C_{12})$cycloalkyl, optionally substituted $(C_4-C_{12})$cycloalkenyl, optionally substituted heterocycle, optionally substituted heteroaryl, optionally substituted mixed ring system, optionally substituted $(C_2-C_{30})$-alkoxy, optionally substituted $(C_2-C_{30})$-ester, polyethyleneimine, poly(glycolic acid), a poly(lactic acid), poly(glycolic-co-lactic acid), chitosan, poly(methacrylic acid), poly(acrylic acid), polycaprolactone, poly(ethylene/vinyl acetate), poly (vinyl acetate), poly(vinyl methyl ether), poly(vinyl alcohol), poly (N-isopropylacrylamide), —OH, a lipid, a saccharide, a polysaccharide, a nucleic acid, an amino acid, a peptide, a peptoid, a fatty acid, ethylene glycol, and polyethylene glycol; $R^7$ is selected from optionally substituted $(C_1-C_{30})$alkyl, optionally substituted $(C_1-C_{30})$heteroalkyl, optionally substituted $(C_1-C_{30})$alkenyl, optionally substituted $(C_1-C_{30})$heteroalkenyl, optionally substituted $(C_1-C_{30})$alkynyl, optionally substituted $(C_1-C_{30})$heteroalkynyl, optionally substituted aryl, optionally substituted $(C_3-C_{12})$cycloalkyl, optionally substituted $(C_4-C_{12})$cycloalkenyl, optionally substituted heterocycle, optionally substituted heteroaryl, optionally substituted mixed ring system, optionally substituted $(C_2-C_{30})$-alkoxy, optionally substituted $(C_2-C_{30})$-ester, polyethyleneimine, poly(glycolic acid), a poly (lactic acid), poly(glycolic-co-lactic acid), chitosan, poly (methacrylic acid), poly(acrylic acid), polycaprolactone, poly(ethylene/vinyl acetate), poly(vinyl acetate), poly(vinyl methyl ether), poly(vinyl alcohol), poly (N-isopropylacrylamide), —OH, a lipid, a saccharide, a polysaccharide, a nucleic acid, an amino acid, a peptide, a peptoid, a fatty acid, ethylene glycol, and polyethylene glycol; and X is a counterion selected from the group consisting of acetate, aspartate, benzenesulfonate, benzoate, besylate, bicarbonate, bitartrate, bromide, camsylate, carbonate, chloride, citrate, decanoate, edetate, esylate, fumarate, gluceptate, gluconate, glutamate, glycolate, hexanoate, hydroxynaphthoate, iodide, isethionate, lactate, lactobionate, malate, maleate, mandelate, mesylate, methylsulfate, mucate, napsylate, nitrate, octanoate, oleate, pamoate, pantothenate, phosphate, polygalacturonate, propionate, salicylate, stearate, succinate, sulfate, tartrate, teoclate and tosylate. In yet a further embodiment, the prodrug comprises the structure of Formula III:

wherein, n is an integer selected from 1 to 400,000, X is a counterion selected from the group consisting of acetate, aspartate, benzenesulfonate, benzoate, besylate, bicarbonate, bitartrate, bromide, camsylate, carbonate, chloride, citrate, decanoate, edetate, esylate, fumarate, gluceptate, gluconate, glutamate, glycolate, hexanoate, hydroxynaphthoate, iodide, isethionate, lactate, lactobionate, malate, maleate, mandelate, mesylate, methylsulfate, mucate, napsylate, nitrate, octanoate, oleate, pamoate, pantothenate, phosphate, polygalacturonate, propionate, salicylate, stearate, succinate, sulfate, tartrate, teoclate and tosylate.

In a certain embodiment, the disclosure also provides for a pharmaceutical composition comprising a prodrug of the disclosure and a pharmaceutically acceptable carrier, diluent, and/or excipient. In a further embodiment, the pharmaceutical composition is formulated for oral or parenteral administration. In yet a further embodiment, the pharmaceutical composition is in the form of enterically coated tablets or capsules.

In a particular embodiment, the disclosure further provides a method of treating a subject with a cancer, comprising: administering a therapeutically effective amount of a prodrug of disclosed herein to the subject in need of treatment thereof. In another embodiment, the cancer is selected from chronic myelogenous leukemia (CML), acute lymphoblastic leukemia (ALL), non-small cell lung cancer (NSCLC), breast cancer, melanoma, colorectal cancer, and ovarian cancer. In yet another embodiment, the prodrug is administered at a dose from 100 mg/kg to 500 mg/kg. In a further embodiment, the prodrug is administered sequentially or concurrently with one or more anticancer therapeutic agents selected from the group consisting of angiogenesis

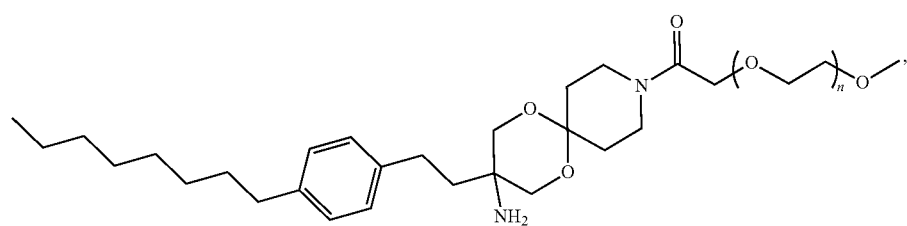

Formula III or a pharmaceutically acceptable salt or solvate thereof, wherein, n is an integer selected from 1 to 400,000. In another embodiment, the prodrug is a pharmaceutically acceptable salt form of the prodrug having the structure of Formula III(a):

inhibitors, tyrosine kinase inhibitors, PARP inhibitors, alkylating agents, vinca alkaloids, anthracyclines, antitumor antibiotics, antimetabolites, topoisomerase inhibitors, aromatase inhibitors, mTor inhibitors, retinoids, and HDAC inhibitors.

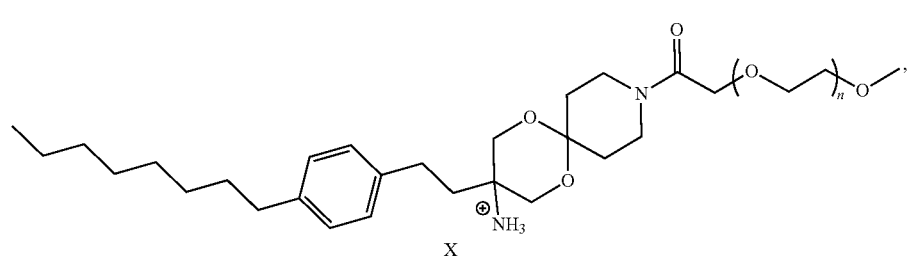

Formula III (a)

In a particular embodiment, the disclosure further provides a method of treating a subject with multiple sclerosis, comprising: administering an effective amount of a prodrug of the disclosure the subject in need of treatment thereof. In a further embodiment, the prodrug is administered sequentially or concurrently with one or more multiple sclerosis treatments selected from the group consisting of beta interferons, glatiramer acetate, dimethyl fumarate, teriflunomide, siponimod, ocrelizumab, natalizumab, alemtuzumab, and mitoxantrone.

DETAILED DESCRIPTION

Figure 1:
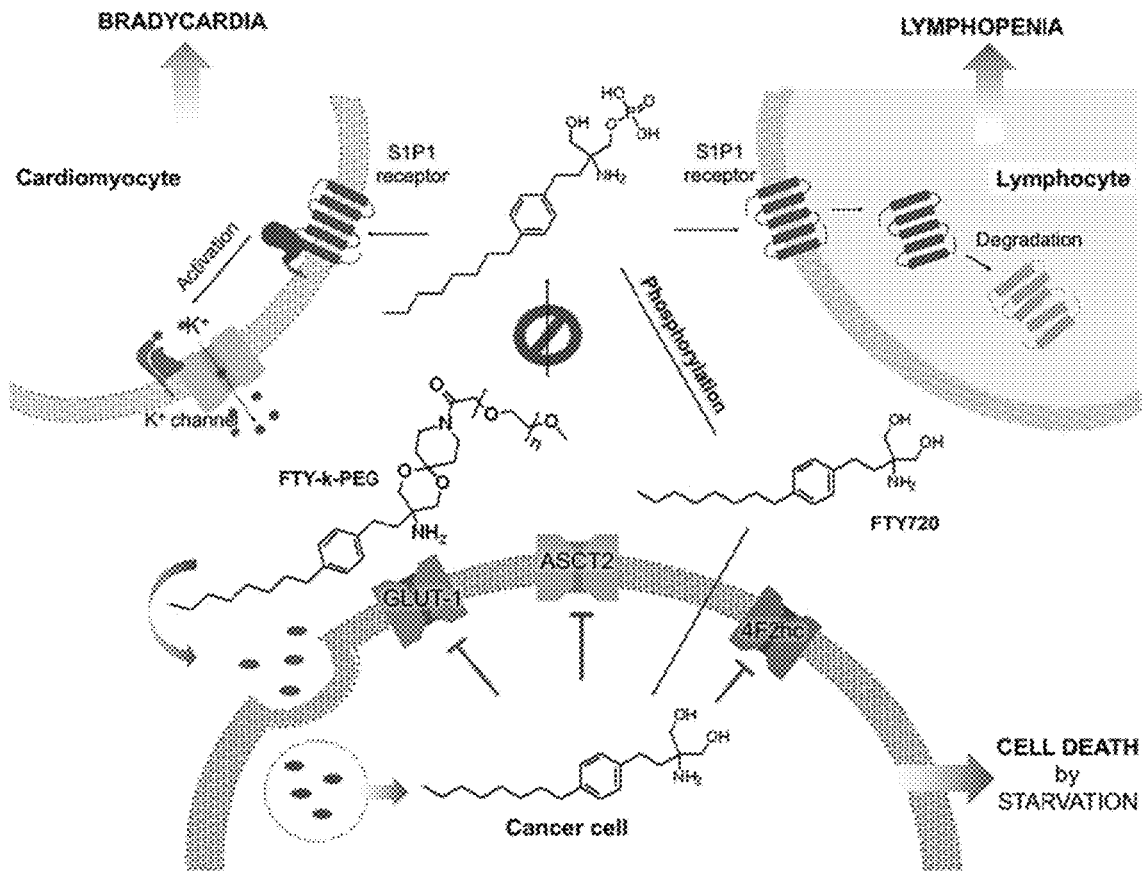
FIG. 1 provides a hypothetical illustration of FTY-k-PEG's mechanism of action. Fingolimod is rapidly phosphorylated to activate S1PRs and subsequently induces bradycardia and lymphopenia at an anti-neoplastic dose. An acid-transforming prodrug formulation shields fingolimod from phosphorylation, while maintaining its efficacy to downregulate nutrient transport proteins once endocytosed and reduced to the anti-neoplastic active drug form.

As used herein and in the appended claims, the singular forms "a," "an," and "the" include plural referents unless the context clearly dictates otherwise. Thus, for example, reference to "a prodrug" includes a plurality of such prodrugs and reference to "the chemotherapeutic agent" includes reference to one or more chemotherapeutic agents and equivalents thereof known to those skilled in the art, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Unless defined otherwise, all technical and scientific terms used herein have the same meaning as commonly understood to one of ordinary skill in the art to which this disclosure belongs. Although many methods and reagents are similar or equivalent to those described herein, the exemplary methods and materials are disclosed herein.

All publications mentioned herein are incorporated herein by reference in full for the purpose of describing and disclosing the methodologies, which might be used in connection with the description herein. Moreover, with respect to any term that is presented in one or more publications that is similar to, or identical with, a term that has been expressly defined in this disclosure, the definition of the term as expressly provided in this disclosure will control in all respects.

It should be understood that this invention is not limited to the particular methodology, protocols, and reagents, etc., described herein and as such may vary. The terminology used herein is for the purpose of describing particular embodiments only and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used to described the present invention, in connection with percentages means±1%.

The term "alkenyl", refers to an organic group that is comprised of carbon and hydrogen atoms that contains at least one double covalent bond between two carbons. Typically, an "alkenyl" as used in this disclosure, refers to organic group that contains 2, 3, 4, 5, 6, 7, 8, 9, 10, 11, 12, 13, 14, 15, 16, 17, 18, 19, 20, or 30 carbon atoms, or any range of carbon atoms between or including any two of the foregoing values. An alkenyl group of three or more carbons can contain more than one double bond. In certain instances, the alkenyl group will be conjugated, in other cases an alkenyl group will not be conjugated, and yet other cases the alkenyl group may have stretches of conjugation and stretches of nonconjugation. Additionally, if there is more than 2 carbon, the carbons may be connected in a linear manner, or alternatively if there are more than 3 carbons then the carbons may also be linked in a branched fashion so that the parent chain contains one or more secondary, tertiary, or quaternary carbons. An alkenyl may be substituted or unsubstituted, unless stated otherwise.

The term "alkyl", refers to an organic group that is comprised of carbon and hydrogen atoms that contains single covalent bonds between carbons. Typically, an "alkyl" as used in this disclosure, refers to an organic group that contains 1, 2, 3, 4, 5, 6, 7, 8, 9, 10, 11, 12, 13, 14, 15, 16, 17, 18, 19, 20, or 30 carbon atoms, or any range of carbon atoms between or including any two of the foregoing values. Where if there is more than 1 carbon, the carbons may be connected in a linear manner, or alternatively if there are more than 2 carbons then the carbons may also be linked in a branched fashion so that the parent chain contains one or more secondary, tertiary, or quaternary carbons. An alkyl may be substituted or unsubstituted, unless stated otherwise.

The term "alkynyl", refers to an organic group that is comprised of carbon and hydrogen atoms that contains a triple covalent bond between two carbons. Typically, an "alkynyl" as used in this disclosure, refers to organic group that contains that contains 2, 3, 4, 5, 6, 7, 8, 9, 10, 11, 12, 13, 14, 15, 16, 17, 18, 19, 20, or 30 carbon atoms, or any range of carbon atoms between or including any two of the foregoing values. An alkynyl group of three or more carbons can contain more than one triple bond. Where if there is more than 3 carbon, the carbons may be connected in a linear manner, or alternatively if there are more than 4 carbons then the carbons may also be linked in a branched fashion so that the parent chain contains one or more secondary, tertiary, or quaternary carbons. An alkynyl may be substituted or unsubstituted, unless stated otherwise.

The term "aryl", as used in this disclosure, refers to a conjugated planar ring system with delocalized pi electron clouds that contain only carbon as ring atoms. An "aryl" for the purposes of this disclosure encompass from 1 to 5 aryl rings wherein when the aryl is greater than 1 ring the aryl rings are joined so that they are linked, fused, or a combination thereof. An aryl may be substituted or unsubstituted, or in the case of more than one aryl ring, one or more rings may be unsubstituted, one or more rings may be substituted, or a combination thereof.

The term generally represented by the notation "$C_x$-$C_y$" (where x and y are whole integers and y>x) prior to a functional group, e.g., "$C_1$-$C_{12}$ alkyl" refers to a number range of carbon atoms. For the purposes of this disclosure any range specified by "$C_x$-$C_y$" (where x and y are whole integers and y>x) is not exclusive to the expressed range, but is inclusive of all possible ranges that include and fall within the range specified by "$C_x$-$C_y$" (where x and y are whole integers and y>x). For example, the term "$C_1$-$C_4$" provides express support for a range of 1 to 4 carbon atoms, but further provides implicit support for ranges encompassed by 1 to 4 carbon atoms, such as 1 to 2 carbon atoms, 1 to 3 carbon atoms, 2 to 3 carbon atoms, 2 to 4 carbon atoms, and 3 to 4 carbon atoms.

The term "cylcloalkenyl", as used in this disclosure, refers to an alkene that contains at least 4 carbon atoms but no more than 12 carbon atoms connected so that it forms a ring. A "cycloalkenyl" for the purposes of this disclosure encompasses from 1 to 4 cycloalkenyl rings, wherein when the cycloalkenyl is greater than 1 ring, then the cycloalkenyl rings are joined so that they are linked, fused, or a combination thereof. A cycloalkenyl may be substituted or unsubstituted, or in the case of more than one cycloalkenyl ring, one or more rings may be unsubstituted, one or more rings may be substituted, or a combination thereof.

The term "cylcloalkyl", as used in this disclosure, refers to an alkyl that contains at least 3 carbon atoms but no more than 12 carbon atoms connected so that it forms a ring. A "cycloalkyl" for the purposes of this disclosure encompasses from 1 to 4 cycloalkyl rings, wherein when the cycloalkyl is greater than 1 ring, then the cycloalkyl rings are joined so that they are linked, fused, or a combination thereof. A cycloalkyl may be substituted or unsubstituted, or in the case of more than one cycloalkyl ring, one or more rings may be unsubstituted, one or more rings may be substituted, or a combination thereof.

The term "hetero-" when used as a prefix, such as, heteroalkyl, hetero-alkenyl, hetero-alkynyl, or hetero-hydrocarbon, for the purpose of this disclosure refers to the specified hydrocarbon having one or more carbon atoms replaced by non-carbon atoms as part of the parent chain. Examples of such non-carbon atoms include, but are not limited to, N, O, S, Si, Al, B, and P. If there is more than one non-carbon atom in the hetero-based parent chain then this atom may be the same element or may be a combination of different elements, such as N and 0.

The term "heterocycle," as used herein, refers to ring structures that contain at least 1 noncarbon ring atom. A "heterocycle" for the purposes of this disclosure encompass from 1 to 5 heterocycle rings, wherein when the heterocycle is greater than 1 ring the heterocycle rings are joined so that they are linked, fused, or a combination thereof. A heterocycle may be aromatic or nonaromatic, or in the case of more than one heterocycle ring, one or more rings may be nonaromatic, one or more rings may be aromatic, or a combination thereof. A heterocycle may be substituted or unsubstituted, or in the case of more than one heterocycle ring one or more rings may be unsubstituted, one or more rings may be substituted, or a combination thereof. Typically, the noncarbon ring atom is N, O, S, Si, Al, B, or P. In the case where there is more than one noncarbon ring atom, these noncarbon ring atoms can either be the same element, or combination of different elements, such as N and O. Examples of heterocycles include, but are not limited to: a monocyclic heterocycle such as, aziridine, oxirane, thiirane, azetidine, oxetane, thietane, pyrrolidine, pyrroline, imidazolidine, pyrazolidine, pyrazoline, dioxolane, sulfolane 2,3-dihydrofuran, 2,5-dihydrofuran tetrahydrofuran, thiophane, piperidine, 1,2,3,6-tetrahydro-pyridine, piperazine, morpholine, thiomorpholine, pyran, thiopyran, 2,3-dihydropyran, tetrahydropyran, 1,4-dihydropyridine, 1,4-dioxane, 1,3-dioxane, dioxane, homopiperidine, 2,3,4,7-tetrahydro-1H-azepine homopiperazine, 1,3-dioxepane, 4,7-dihydro-1,3-dioxepin, and hexamethylene oxide; and polycyclic heterocycles such as, indole, indoline, isoindoline, quinoline, tetrahydroquinoline, isoquinoline, tetrahydroisoquinoline, 1,4-benzodioxan, coumarin, dihydrocoumarin, benzofuran, 2,3-dihydrobenzofuran, isobenzofuran, chromene, chroman, isochroman, xanthene, phenoxathiin, thianthrene, indolizine, isoindole, indazole, purine, phthalazine, naphthyridine, quinoxaline, quinazoline, cinnoline, pteridine, phenanthridine, perimidine, phenanthroline, phenazine, phenothiazine, phenoxazine, 1,2-benzisoxazole, benzothiophene, benzoxazole, benzthiazole, benzimidazole, benztriazole, thioxanthine, carbazole, carboline, acridine, pyrolizidine, and quinolizidine. In addition to the polycyclic heterocycles described above, heterocycle includes polycyclic heterocycles wherein the ring fusion between two or more rings includes more than one bond common to both rings and more than two atoms common to both rings. Examples of such bridged heterocycles include quinuclidine, diazabicyclo[2.2.1]heptane and 7-oxabicyclo[2.2.1]heptane.

The terms "heterocyclic group", "heterocyclic moiety", "heterocyclic", or "heterocyclo" used alone or as a suffix or prefix, refers to a heterocycle that has had one or more hydrogens removed therefrom.

The term "substituent" refers to an atom or group of atoms substituted in place of a hydrogen atom, e.g., a boronic acid group. For purposes of this invention, a substituent would include deuterium atoms. Examples of substituents include, but are not limited to, halo (e.g., F, Cl, Br or I), optionally substituted oxygen containing functional group (e.g., alcohol, ketone, aldehyde, acyl halide, carbonate, carboxylic acid, ester, and ether), optionally substituted nitrogen containing functional group (e.g., amide, amine, imine, azide, cyanate, azo, nitrate, nitrile, nitro, and nitroso), optionally substituted sulfur containing functional group (e.g., thiol, sulfide, disulfide, sulfoxide, sulfone, sulfinic acid, sulfonic acid, thiocyanate, thione, and thial), optionally substituted phosphorous containing functional group (e.g., phosphine, phosphonic acid, phosphate, phosphodiester), optionally substituted boron containing functional group (e.g., boronic acid, and boronic ester). Further examples of substituents include, but are not limited to, aryl, heterocycle, alkyl, heteroalkyl, alkenyl, heteroalkenyl, alkynyl, heteroalkynyl, cycloalkyl, alkoxy, ester, halo, hydroxyl, anhydride, carbonyl, carboxyl, carbonate, carboxylate, aldehyde, boronic acid, boronic ester, haloformyl, ester, hydroperoxy, peroxy, ether, orthoester, carboxamide, amine, imine, imide, azide, azo, cyanate, isocyanate, nitrate, nitrite, isonitrile, nitroso, nitro, nitrosooxy, pyridyl, sulfide, disulfide, sulfinyl, sulfo, thiocyanate, isothiocyanate, carbonothioyl, phosphino, phosphono, and phosphate.

The term "mixed ring system" refers to optionally substituted ring structures that contain at least two rings, and wherein the rings are joined together by linking, fusing, or a combination thereof. A mixed ring system comprises a combination of different ring types, including cycloalkyl, cycloalkenyl, aryl, and heterocycle.

The term "substituted" with respect to hydrocarbons, heterocycles, and the like, refers to structures wherein the parent chain contains one or more substituents.

The term "unsubstituted" with respect to hydrocarbons, heterocycles, and the like, refers to structures wherein the parent chain contains no substituents.

For purposes of the disclosure the term "cancer" will be used to encompass cell proliferative disorders, neoplasms, precancerous cell disorders and cancers, unless specifically delineated otherwise. Thus, a "cancer" refers to any cell that undergoes aberrant cell proliferation that can lead to metastasis or tumor growth. Exemplary cancers include but are not limited to, adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, urinary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodermal tumors, visual pathway and hypothalamic glioma, breast cancer, including triple negative breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, soft tissue sarcoma, uterine cancer, uterine sarcoma, skin cancer (non-melanoma), skin cancer (melanoma), papillomas, actinic keratosis and keratoacanthomas, merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor. In a particular embodiment, the cancer is selected from the group consisting of chronic myelogenous leukemia (CML), acute lymphoblastic leukemia (ALL), non-small cell lung cancer (NSCLC), breast cancer, melanoma, colorectal cancer, and ovarian cancer.

While modern medicine has made great advances in the fight against highly challenging diseases such as cancer, a need for specificity remains. Chemotherapeutics target cellular processes which are ubiquitously required, albeit to different extents, in all cells, thereby killing a subset of healthy cells and causing adverse side effects. Furthermore, these side effects severely impact patient quality of life, at times resulting in discontinuation of therapy. Enhancing specificity through conjugation of targeting molecules, exploiting tumor microenvironment, and immunotherapy show much promise in addressing systemic toxicity. However, each strategy may depend upon the particular cancer type and patient's genetic profile, further increasing complexity in development and administration.

A majority of targeted therapies are designed to interfere with a specific component of an oncogenic pathway: however, targets are not always specific to cancer and resistance mechanisms may activate parallel signaling pathways to allow for survival. Cancer metabolism is an attractive therapeutic target since oncogene-driven anabolism, dysregulation of growth, and defects in autophagy sensitize cancer cells to nutrient deprivation. Cancer cells continue biosynthesis despite nutrient deprivation, which eventually limits ATP production and induces bioenergetic stress, ultimately resulting in cell death. Recent studies have reported that fingolimod (Gilenye), an FDA-approved drug for multiple sclerosis, effectively inhibits cancer progression via down-regulation of key nutrient transporters (GLUT1, ASCT2, LAT-1, and 4F2hc) and activation of protein phosphatase 2A (PP2A). Importantly, fingolimod has shown minimal toxicity against normal cells while effectively killing cancer cells. Under the nutrient-limiting conditions induced by fingolimod, normal cells can adapt by undergoing cell cycle arrest to become quiescent and catabolic, thus maintaining survival. Although various therapies currently exist that limit access to nutrients such as angiogenesis inhibitors and L-asparaginase, many do not possess the broad applicability of fingolimod.

Despite its high specificity and efficacy, clinical use of fingolimod for cancer therapy is restricted due to its capability of inducing profound bradycardia at an anti-neoplastic dose. fingolimod is rapidly phosphorylated and becomes an agonist for G protein-coupled sphingosine 1 phosphate receptors (S1PRs), activating a signaling cascade in atrial myocytes that reduces heart rate. Furthermore, phosphorylated fingolimod is also known to induce immunosuppression by inhibiting lymphocyte egress from the thymus and secondary lymphoid organs, resulting in lymphopenia, a reduction of peripheral lymphocytes. Fingolimod analogues designed to prevent phosphorylation through conformational restraint were shown to eliminate these adverse effects. The analogues down-regulate nutrient transport proteins and demonstrate potent anti-cancer efficacy in leukemia and prostate cancer models while maintaining normal heart rate. The promise of these compounds as anti-cancer therapies is counterbalanced by high monetary and temporal investments for new drug development. FDA approval, including clinical trials, may take up more than a decade with costs averaging over $1 billion and approval rate nearing only 10%. Most importantly, this approach is generalizable to other chemotherapeutic agents. Prodrug formulation presents a less costly alternative through the 505(b)(2) development process, which could take as few as 30 months for FDA-approval. Therefore, a generalized approach to the development of prodrug to specifically eliminate side effects of an already approved drug is highly meritorious from a scientific and translational standpoint.

Phosphorylation of fingolimod can occur during circulation. Prodrugs of fingolimod were developed herein that were stable in the bloodstream, i.e., not phosphorylated. The prodrugs of the disclosure were developed by conjugating fingolimod with a biocompatible polymer, polyethylene glycol (PEG), via an acid-labile linkage. The prodrugs of the disclosure avoid bradycardia and immunosuppression by limiting phosphorylation (e.g., see FIG. 1). Once taken up by a cancer cell via endocytosis the prodrug transforms to its active drug in the mildly acidic endosome and induce cell death by starvation. Both in vitro and in vivo studies demonstrated that the novel molecular approach in this study address a key clinical demand in developing effective and safe cancer chemotherapeutics.

The disclosure provides for a prodrug of fingolimod comprising a stimuli-responsive linker that is cleavable when exposed to environmental stimuli (e.g., acidic environment, basic environment, reducing environment, etc.), external stimuli (e.g., heat, ultrasound, photo-irradiation, an electrochemical field, a magnetic field, etc.), or specific biological processes (e.g., enzymatic cleavage, ion chelation, etc.) to form the active drug fingolimod. In a particular embodiment, a prodrug of the disclosure is fully converted to fingolimod when exposed to a pH from 4.5 to 6.5, i.e., environments found in lysosomes and endosomes.

In a certain embodiment, the disclosure provides for a prodrug that comprises the structure of Formula I(a) or Formula I(b):

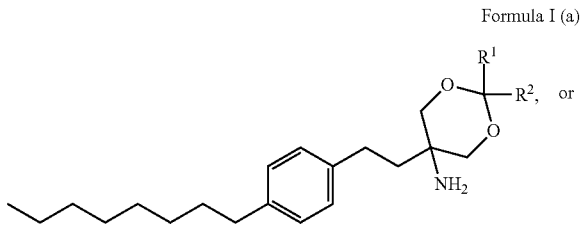

Formula I(a)

-continued

Formula I (b)

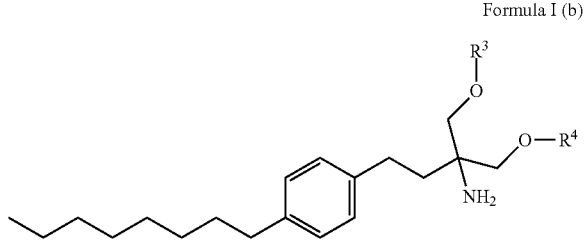

or a pharmaceutically acceptable salt or solvate thereof, wherein,

R¹ is selected from H, D,

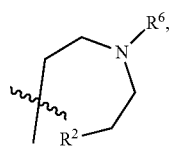

optionally substituted $(C_1-C_{30})$ alkyl, optionally substituted $(C_1-C_{30})$ heteroalkyl, optionally substituted $(C_1-C_{30})$alkenyl, optionally substituted $(C_1-C_{30})$heteroalkenyl, optionally substituted $(C_1-C_{30})$alkynyl, optionally substituted $(C_1-C_{30})$heteroalkynyl, optionally substituted aryl, optionally substituted $(C_3-C_{12})$cycloalkyl, optionally substituted $(C_4-C_{12})$cycloalkenyl, optionally substituted heterocycle, optionally substituted heteroaryl, optionally substituted mixed ring system, optionally substituted $(C_2-C_{30})$-alkoxy, optionally substituted $(C_2-C_{30})$-ester, polyethyleneimine, poly(glycolic acid), a poly(lactic acid), poly(glycolic-co-lactic acid), chitosan, poly(methacrylic acid), poly(acrylic acid), polycaprolactone, poly(ethylene/vinyl acetate), poly(vinyl acetate), poly(vinyl methyl ether), poly(vinyl alcohol), poly (N-isopropylacrylamide), —OH, a lipid, a saccharide, a polysaccharide, a nucleic acid, an amino acid, a peptide, a peptoid, a fatty acid, ethylene glycol, and polyethylene glycol;

R² is selected from

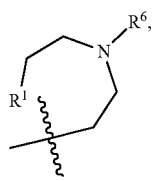

optionally substituted $(C_1-C_{30})$alkyl, optionally substituted $(C_1-C_{30})$heteroalkyl, optionally substituted $(C_1-C_{30})$alkenyl, optionally substituted $(C_1-C_{30})$heteroalkenyl, optionally substituted $(C_1-C_{30})$alkynyl, optionally substituted $(C_1-C_{30})$ heteroalkynyl, optionally substituted aryl, optionally substituted $(C_3-C_{12})$cycloalkyl, optionally substituted $(C_4-C_{12})$ cycloalkenyl, optionally substituted heterocycle, optionally substituted heteroaryl, optionally substituted mixed ring system, optionally substituted $(C_2-C_{30})$-alkoxy, optionally substituted $(C_2-C_{30})$-ester, polyethyleneimine, poly(glycolic acid), a poly(lactic acid), poly(glycolic-co-lactic acid), chitosan, poly(methacrylic acid), poly(acrylic acid), polycaprolactone, poly(ethylene/vinyl acetate), poly(vinyl acetate), poly(vinyl methyl ether), poly(vinyl alcohol), poly (N-isopropylacrylamide), —OH, a lipid, a saccharide, a polysaccharide, a nucleic acid, an amino acid, a peptide, a peptoid, a fatty acid, ethylene glycol, and polyethylene glycol;

R³ and R⁴ are independently selected from

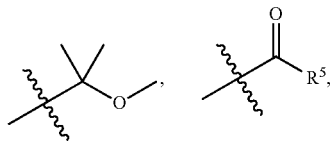

optionally substituted $(C_1-C_{30})$alkyl, optionally substituted $(C_1-C_{30})$ heteroalkyl, optionally substituted $(C_1-C_{30})$ alkenyl, optionally substituted $(C_1-C_{30})$heteroalkenyl, optionally substituted $(C_1-C_{30})$alkynyl, optionally substituted $(C_1-C_{30})$heteroalkynyl, optionally substituted aryl, optionally substituted $(C_3-C_{12})$cycloalkyl, optionally substituted $(C_4-C_{12})$cycloalkenyl, optionally substituted heterocycle, optionally substituted heteroaryl, optionally substituted mixed ring system, optionally substituted $(C_2-C_{30})$-alkoxy, optionally substituted $(C_2-C_{30})$-ester, polyethyleneimine, poly(glycolic acid), a poly(lactic acid), poly(glycolic-co-lactic acid), chitosan, poly(methacrylic acid), poly(acrylic acid), polycaprolactone, poly(ethylene/vinyl acetate), poly(vinyl acetate), poly(vinyl methyl ether), poly(vinyl alcohol), poly (N-isopropylacrylamide), a lipid, a saccharide, a polysaccharide, a nucleic acid, an amino acid, a peptide, a peptoid, a fatty acid, ethylene glycol, and polyethylene glycol; and R⁵ is selected from optionally substituted $(C_1-C_{30})$alkyl, optionally substituted $(C_1-C_{30})$heteroalkyl, optionally substituted $(C_1-C_{30})$ alkenyl, optionally substituted $(C_1-C_{30})$ heteroalkenyl, optionally substituted $(C_1-C_{30})$alkynyl, optionally substituted $(C_1-C_{30})$heteroalkynyl, optionally substituted aryl, optionally substituted $(C_3-C_{12})$cycloalkyl, optionally substituted $(C_4-C_{12})$cycloalkenyl, optionally substituted heterocycle, optionally substituted heteroaryl, optionally substituted mixed ring system, optionally substituted $(C_2-C_{30})$-alkoxy, optionally substituted $(C_2-C_{30})$-ester, polyethyleneimine, poly(glycolic acid), a poly(lactic acid), poly(glycolic-co-lactic acid), chitosan, poly(methacrylic acid), poly(acrylic acid), polycaprolactone, poly(ethylene/vinyl acetate), poly(vinyl acetate), poly(vinyl methyl ether), poly(vinyl alcohol), poly (N-isopropylacrylamide), —OH, a lipid, a saccharide, a polysaccharide, a nucleic acid, an amino acid, a peptide, a peptoid, a fatty acid, ethylene glycol, and polyethylene glycol;

R⁶ is selected from H, D,

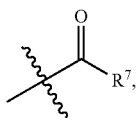

optionally substituted $(C_1-C_{30})$alkyl, optionally substituted $(C_1-C_{30})$heteroalkyl, optionally substituted $(C_1-C_{30})$alkenyl, optionally substituted $(C_1-C_{30})$heteroalkenyl, optionally substituted $(C_1-C_{30})$alkynyl, optionally substituted $(C_1-C_{30})$ heteroalkynyl, optionally substituted aryl, optionally substituted $(C_3-C_{12})$cycloalkyl, optionally substituted $(C_4-C_{12})$ cycloalkenyl, optionally substituted heterocycle, optionally substituted heteroaryl, optionally substituted mixed ring system, optionally substituted $(C_2-C_{30})$-alkoxy, optionally substituted (C₂-C₃₀)-ester, polyethyleneimine, poly(glycolic acid), a poly(lactic acid), poly(glycolic-co-lactic acid), chitosan, poly(methacrylic acid), poly(acrylic acid), polycaprolactone, poly(ethylene/vinyl acetate), poly(vinyl acetate), poly(vinyl methyl ether), poly(vinyl alcohol), poly (N-isopropylacrylamide), —OH, a lipid, a saccharide, a polysaccharide, a nucleic acid, an amino acid, a peptide, a peptoid, a fatty acid, ethylene glycol, and polyethylene glycol; and R⁷ is selected from optionally substituted (C₁-C₃₀)alkyl, optionally substituted (C₁-C₃₀)heteroalkyl, optionally substituted (C₁-C₃₀) alkenyl, optionally substituted (C₁-C₃₀)heteroalkenyl, optionally substituted (C₁-C₃₀)alkynyl, optionally substituted (C₁-C₃₀)heteroalkynyl, optionally substituted aryl, optionally substituted (C₃-C₁₂)cycloalkyl, optionally substituted (C₄-C₁₂)cycloalkenyl, optionally substituted heterocycle, optionally substituted heteroaryl, optionally substituted mixed ring system, optionally substituted (C₂-C₃₀)-alkoxy, optionally substituted (C₂-C₃₀)-ester, polyethyleneimine, poly(glycolic acid), a poly(lactic acid), poly(glycolic-co-lactic acid), chitosan, poly(methacrylic acid), poly(acrylic acid), polycaprolactone, poly(ethylene/vinyl acetate), poly(vinyl acetate), poly(vinyl methyl ether), poly(vinyl alcohol), poly (N-isopropylacrylamide), —OH, a lipid, a saccharide, a polysaccharide, a nucleic acid, an amino acid, a peptide, a peptoid, a fatty acid, ethylene glycol, and polyethylene glycol.

In a particular embodiment, the disclosure also provides for a prodrug that comprises the structure of Formula II:

Formula II

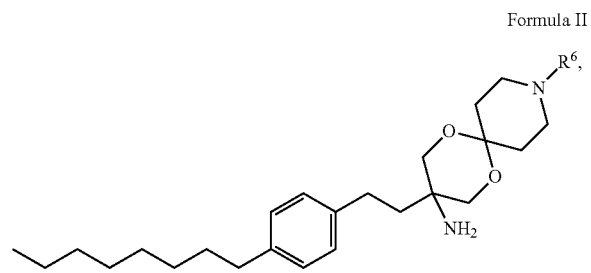

or a pharmaceutically acceptable salt or solvate thereof,
wherein, R⁶ is selected from H, D,

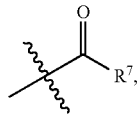

optionally substituted (C₁-C₃₀)alkyl, optionally substituted (C₁-C₃₀)heteroalkyl, optionally substituted (C₁-C₃₀)alkenyl, optionally substituted (C₁-C₃₀)heteroalkenyl, optionally substituted (C₁-C₃₀)alkynyl, optionally substituted (C₁-C₃₀) heteroalkynyl, optionally substituted aryl, optionally substituted (C₃-C₁₂)cycloalkyl, optionally substituted (C₄-C₁₂)cycloalkenyl, optionally substituted heterocycle, optionally substituted heteroaryl, optionally substituted mixed ring system, optionally substituted (C₂-C₃₀)-alkoxy, optionally substituted (C₂-C₃₀)-ester, polyethyleneimine, poly(glycolic acid), a poly(lactic acid), poly(glycolic-co-lactic acid), chitosan, poly(methacrylic acid), poly(acrylic acid), polycaprolactone, poly(ethylene/vinyl acetate), poly(vinyl acetate), poly(vinyl methyl ether), poly(vinyl alcohol), poly (N-isopropylacrylamide), —OH, a lipid, a saccharide, a polysaccharide, a nucleic acid, an amino acid, a peptide, a peptoid, a fatty acid, ethylene glycol, and polyethylene glycol; and R⁷ is selected from an optionally substituted (C₁-C₃₀) alkyl, optionally substituted (C₁-C₃₀)heteroalkyl, optionally substituted (C₁-C₃₀) alkenyl, optionally substituted (C₁-C₃₀) heteroalkenyl, optionally substituted (C₁-C₃₀)alkynyl, optionally substituted (C₁-C₃₀)heteroalkynyl, optionally substituted aryl, optionally substituted (C₃-C₁₂)cycloalkyl, optionally substituted (C₄-C₁₂)cycloalkenyl, optionally substituted heterocycle, optionally substituted heteroaryl, optionally substituted mixed ring system, optionally substituted (C₂-C₃₀)-alkoxy, optionally substituted (C₂-C₃₀)-ester, polyethyleneimine, poly(glycolic acid), a poly(lactic acid), poly(glycolic-co-lactic acid), chitosan, poly(methacrylic acid), poly(acrylic acid), polycaprolactone, poly(ethylene/vinyl acetate), poly(vinyl acetate), poly(vinyl methyl ether), poly(vinyl alcohol), poly (N-isopropylacrylamide), —OH, a lipid, a saccharide, a polysaccharide, a nucleic acid, an amino acid, a peptide, a peptoid, a fatty acid, ethylene glycol, and polyethylene glycol.

In a further embodiment, the disclosure provides for a pharmaceutically acceptable salt form of the prodrug having the structure of Formula II(a):

Formula II (a)

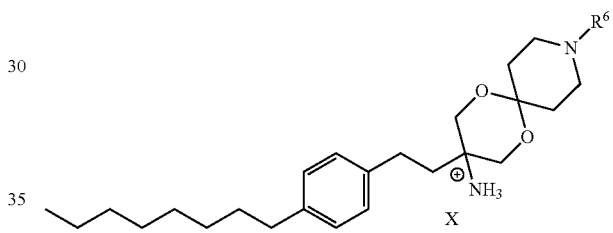

wherein,
R⁶ is selected from H, D,

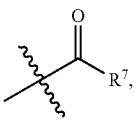

optionally substituted (C₁-C₃₀)alkyl, optionally substituted (C₁-C₃₀)heteroalkyl, optionally substituted (C₁-C₃₀)alkenyl, optionally substituted (C₁-C₃₀)heteroalkenyl, optionally substituted (C₁-C₃₀)alkynyl, optionally substituted (C₁-C₃₀) heteroalkynyl, optionally substituted aryl, optionally substituted (C₃-C₁₂)cycloalkyl, optionally substituted (C₄-C₁₂) cycloalkenyl, optionally substituted heterocycle, optionally substituted heteroaryl, optionally substituted mixed ring system, optionally substituted (C₂-C₃₀)-alkoxy, optionally substituted (C₂-C₃₀)-ester, polyethyleneimine, poly(glycolic acid), a poly(lactic acid), poly(glycolic-co-lactic acid), chitosan, poly(methacrylic acid), poly(acrylic acid), polycaprolactone, poly(ethylene/vinyl acetate), poly(vinyl acetate), poly(vinyl methyl ether), poly(vinyl alcohol), poly (N-isopropylacrylamide), —OH, a lipid, a saccharide, a polysaccharide, a nucleic acid, an amino acid, a peptide, a peptoid, a fatty acid, ethylene glycol, and polyethylene glycol;

R⁷ is selected from optionally substituted (C₁-C₃₀)alkyl, optionally substituted (C₁-C₃₀)heteroalkyl, optionally substituted (C₁-C₃₀) alkenyl, optionally substituted (C₁-C₃₀)

heteroalkenyl, optionally substituted (C$_1$-C$_{30}$)alkynyl, optionally substituted (C$_1$-C$_{30}$)heteroalkynyl, optionally substituted aryl, optionally substituted (C$_3$-C$_{12}$)cycloalkyl, optionally substituted (C$_4$-C$_{12}$)cycloalkenyl, optionally substituted heterocycle, optionally substituted heteroaryl, optionally substituted mixed ring system, optionally substituted (C$_2$-C$_{30}$)-alkoxy, optionally substituted (C$_2$-C$_{30}$)-ester, polyethyleneimine, poly(glycolic acid), a poly(lactic acid), poly(glycolic-co-lactic acid), chitosan, poly(methacrylic acid), poly(acrylic acid), polycaprolactone, poly(ethylene/vinyl acetate), poly(vinyl acetate), poly(vinyl methyl ether), poly(vinyl alcohol), poly (N-isopropylacrylamide), —OH, a lipid, a saccharide, a polysaccharide, a nucleic acid, an amino acid, a peptide, a peptoid, a fatty acid, ethylene glycol, and polyethylene glycol; and X is a counterion selected from the group consisting of acetate, aspartate, benzenesulfonate, benzoate, besylate, bicarbonate, bitartrate, bromide, camsylate, carbonate, chloride, citrate, decanoate, edetate, esylate, fumarate, gluceptate, gluconate, glutamate, glycolate, hexanoate, hydroxynaphthoate, iodide, isethionate, lactate, lactobionate, malate, maleate, mandelate, mesylate, methylsulfate, mucate, napsylate, nitrate, octanoate, oleate, pamoate, pantothenate, phosphate, polygalacturonate, propionate, salicylate, stearate, succinate, sulfate, tartrate, teoclate and tosylate.

In a certain embodiment, the disclosure further provides for a prodrug that comprises the structure of Formula III:

hydroxynaphthoate, iodide, isethionate, lactate, lactobionate, malate, maleate, mandelate, mesylate, methylsulfate, mucate, napsylate, nitrate, octanoate, oleate, pamoate, pantothenate, phosphate, polygalacturonate, propionate, salicylate, stearate, succinate, sulfate, tartrate, teoclate and tosylate.

The disclosure further provides for a pharmaceutical composition comprising a prodrug disclosed herein. Any of a variety of art-known methods can be used to administer a prodrug disclosed herein. For example, administration can be parenterally, by injection or by gradual infusion over time. The prodrugs alone or with the other therapeutic agents can be administered orally, intravenously, intraperitoneally, intramuscularly, subcutaneously, intracavity, by inhalation, or transdermally.

A pharmaceutical composition comprising a prodrug of the disclosure can be in a form suitable for administration to a subject using carriers, excipients, diluents and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol, and polyhydric alcohols. Intravenous vehicles include fluid and nutrient replenishers. Preservatives include antimicrobial, chelating agents, and inert gases. Other pharmaceutically acceptable carriers include aqueous solutions, non-toxic excipients, including salts, preserva-

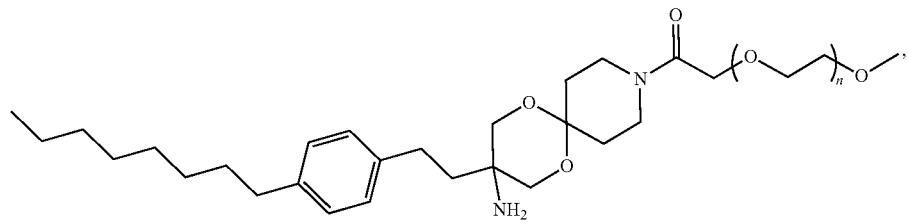

Formula III or a pharmaceutically acceptable salt or solvate thereof, wherein, n is an integer selected from 1 to 400,000.

In a further embodiment, the disclosure provides for a pharmaceutically acceptable salt form of the prodrug having the structure of Formula III(a):

tives, buffers and the like, as described, for instance, in Remington's Pharmaceutical Sciences, 15th ed., Easton: Mack Publishing Co., 1405-1412, 1461-1487 (1975), and The National Formulary XIV., 14th ed., Washington: American Pharmaceutical Association (1975), the contents of

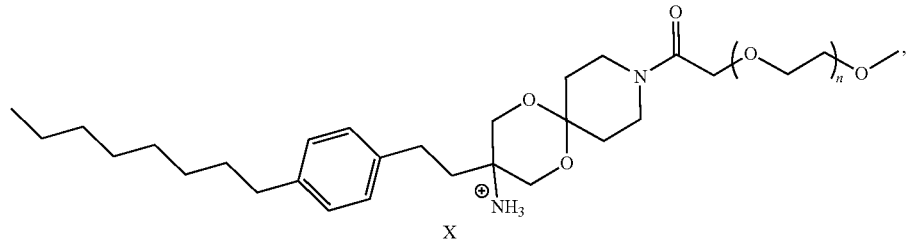

Formula III (a)

wherein, n is an integer selected from 1 to 400,000,

X is a counterion selected from the group consisting of acetate, aspartate, benzenesulfonate, benzoate, besylate, bicarbonate, bitartrate, bromide, camsylate, carbonate, chloride, citrate, decanoate, edetate, esylate, fumarate, gluceptate, gluconate, glutamate, glycolate, hexanoate, which are hereby incorporated by reference. The pH and exact concentration of the various components of the pharmaceutical composition are adjusted according to routine skills in the art. See Goodman and Gilman's, The Pharmacological Basis for Therapeutics (7th ed.).

The disclosure further provides for a pharmaceutical composition comprising a prodrug disclosed herein that can be administered in a convenient manner, such as by injection (subcutaneous, intravenous, etc.), oral administration, inhalation, transdermal application, or rectal administration. Depending on the route of administration, the pharmaceutical composition can be coated with a material to protect the pharmaceutical composition from the action of enzymes, acids, and other natural conditions that may inactivate the pharmaceutical composition. The pharmaceutical composition can also be administered parenterally or intraperitoneally. Dispersions can also be prepared in glycerol, liquid polyethylene glycols, and mixtures thereof, and in oils. Under ordinary conditions of storage and use, these preparations may contain a preservative to prevent the growth of microorganisms.

A "pharmaceutically acceptable carrier" is intended to include solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the pharmaceutical composition, use thereof in the therapeutic compositions and methods of treatment is contemplated. Supplementary active compounds can also be incorporated into the compositions.

The pharmaceutical composition can be orally administered, for example, with an inert diluent or an assimilable edible carrier. The pharmaceutical composition and other ingredients can also be enclosed in a hard or soft-shell gelatin capsule, compressed into tablets, or incorporated directly into the individual's diet. For oral therapeutic administration, the pharmaceutical composition can be incorporated with excipients and used in the form of ingestible tablets, buccal tablets, troches, capsules, elixirs, suspensions, syrups, wafers, chewable tablets, gummies, and the like. Such compositions and preparations should contain at least 1% by weight of active compound. The percentage of the compositions and preparations can, of course, be varied and can conveniently be between about 5% to about 80% of the weight of the unit.

The tablets, troches, pills, capsules, and the like can also contain the following: a binder, such as gum gragacanth, acacia, corn starch, or gelatin; excipients such as dicalcium phosphate; a disintegrating agent, such as corn starch, potato starch, alginic acid, and the like; a lubricant, such as magnesium stearate; and a sweetening agent, such as sucrose, lactose or saccharin, or a flavoring agent such as peppermint, oil of wintergreen, or cherry flavoring. When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar, or both. A syrup or elixir can contain the agent, sucrose as a sweetening agent, methyl and propylparabens as preservatives, a dye, and flavoring, such as cherry or orange flavor. Of course, any material used in preparing any dosage unit form should be pharmaceutically pure and substantially non-toxic/biocompatible in the amounts employed. In addition, the pharmaceutical composition can be incorporated into sustained-release preparations and formulations.

In further embodiments, the disclosure further provides that oral pharmaceutical formulations comprising a prodrug disclosed herein may have an enteric coating. As used herein "enteric coating", is a material, a polymer material or materials which encase the medicament core (e.g., prodrug the disclosure). Typically, a substantial amount or all of the enteric coating material is dissolved before the medicament or therapeutically active agent is released from the dosage form, so as to achieve delayed dissolution of the medicament core. A suitable pH-sensitive polymer is one which will dissolve in intestinal juices at a higher pH level (pH greater than 6), such as within the small intestine and therefore permit release of the pharmacologically active substance in the regions of the small intestine and not in the upper portion of the GI tract, such as the stomach. An "enterically coated" drug or tablet refers to a drug or tablet that is coated with a substance—i.e., with an "enteric coating"—that remains intact in the stomach but dissolves and releases the drug once the small intestine is reached.

The coating material is selected such that the therapeutically active agent will be released when the dosage form reaches the small intestine or a region in which the pH is greater than pH 6. The coating may be a pH-sensitive material, which remains intact in the lower pH environs of the stomach, but which disintegrate or dissolve at a more neutral pH commonly found in the small intestine of the patient. For example, the enteric coating material begins to dissolve in an aqueous solution at pH between about 6 to about 7.4. For example, pH-sensitive materials will not undergo significant dissolution until the dosage form has emptied from the stomach and proximal portions of the small intestine. The pH of the small intestine gradually increases to about 6.5 in the duodenal bulb to about 7.2 in the distal portions of the small intestine (ileum).

Enteric coatings have been used for many years to arrest the release of the drug from orally ingestible dosage forms. Depending upon the composition and/or thickness, the enteric coatings are resistant to stomach acid for required periods of time before they begin to disintegrate and permit release of the drug in the lower stomach or upper part of the small intestines. Examples of some enteric coatings are disclosed in U.S. Pat. No. 5,225,202 which is incorporated by reference fully herein. As set forth in U.S. Pat. No. 5,225,202, some examples of coating previously employed are beeswax and glyceryl monostearate; beeswax, shellac and cellulose; and cetyl alcohol, mastic and shellac, as well as shellac and stearic acid (U.S. Pat. No. 2,809,918); polyvinyl acetate and ethyl cellulose (U.S. Pat. No. 3,835,221); and neutral copolymer of polymethacrylic acid esters (Eudragit L30D) (F. W. Goodhart et al., Pharm. Tech., pp. 64-71, April 1984); copolymers of methacrylic acid and methacrylic acid methylester (Eudragits), or a neutral copolymer of polymethacrylic acid esters containing metallic stearates (Mehta et al., U.S. Pat. Nos. 4,728,512 and 4,794,001). Such coatings comprise mixtures of fats and fatty acids, shellac and shellac derivatives and the cellulose acid phthalates, e.g., those having a free carboxyl content. See, Remington's at page 1590, and Zeitova et al. (U.S. Pat. No. 4,432,966), for descriptions of suitable enteric coating compositions.

Generally, the enteric coating comprises a polymeric material that prevents prodrug release in the low pH and mildly acidic environment of the stomach and proximal small intestine but that ionizes at a higher pH, typically at a pH of 6 or higher, and thus dissolves sufficiently in the mid to lower small intestines to gradually release the active agent therein. Accordingly, among the most effective enteric coating materials are polyacids having a $pK_a$ in the range of about 3 to 6. Suitable enteric coating materials include, but are not limited to, polymerized gelatin, shellac, methacrylic acid copolymer type C NF, cellulose butyrate phthalate, cellulose hydrogen phthalate, cellulose proprionate phthalate, polyvinyl acetate phthalate (PVAP), cellulose acetate phthalate (CAP), cellulose acetate trimellitate (CAT), hydroxypropyl methylcellulose phthalate, hydroxypropyl methylcellulose acetate, dioxypropyl methylcellulose succinate, carboxymethyl ethylcellulose (CMEC), hydroxypropyl methylcellulose acetate succinate (HPMCAS), and acrylic acid polymers and copolymers, typically formed from methyl acrylate, ethyl acrylate, methyl methacrylate and/or ethyl methacrylate with copolymers of acrylic and methacrylic acid esters (Eudragit NE, Eudragit RL, Eudragit RS). For example, the enterically coating can comprise Eudragit L30D, triethylcitrate, and hydroxypropylmethylcellulose (HPMC), Cystagon® (or other cysteamine derivative), wherein the coating comprises 10 to 13% of the final product.

Preparations for parenteral administration of a composition comprising a prodrug of the disclosure include sterile aqueous or non-aqueous solutions, suspensions, and emulsions. Examples of non-aqueous solvents are propylene glycol, polyethylene glycol, vegetable oils (e.g., olive oil), and injectable organic esters such as ethyl oleate. Examples of aqueous carriers include water, saline, and buffered media, alcoholic/aqueous solutions, and emulsions or suspensions. Examples of parenteral vehicles include sodium chloride solution, Ringer's dextrose, dextrose and sodium chloride, lactated Ringer's, and fixed oils. Intravenous vehicles include fluid and nutrient replenishers, electrolyte replenishers (such as those based on Ringer's dextrose), and the like. Preservatives and other additives such as, other antimicrobial, anti-oxidants, cheating agents, inert gases and the like also can be included.

Pharmaceutical compositions suitable for injectable use include sterile aqueous solutions (where water soluble) or dispersions and sterile powders for the extemporaneous preparation of sterile injectable solutions or dispersions. In all cases, the composition should be sterile and should be fluid to the extent that easy syringability exists. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size, in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, it will be typical to include isotonic agents, for example, sugars, polyalcohols, such as mannitol, sorbitol, or sodium chloride in the composition. Prolonged absorption of the injectable compositions can be brought about by including in the composition an agent that delays absorption, for example, aluminum monostearate and gelatin.

Sterile injectable solutions can be prepared by incorporating the pharmaceutical composition in the required amount in an appropriate solvent with one or a combination of ingredients enumerated above, as required, followed by filtered sterilization. Generally, dispersions are prepared by incorporating the pharmaceutical composition into a sterile vehicle that contains a basic dispersion medium and the required other ingredients from those enumerated above.

It is especially advantageous to formulate parenteral compositions in dosage unit form for ease of administration and uniformity of dosage. "Dosage unit form" as used herein, refers to physically discrete units suited as unitary dosages for the individual to be treated; each unit containing a predetermined quantity of pharmaceutical composition is calculated to produce the desired therapeutic effect in association with the required pharmaceutical carrier. The specification for the dosage unit forms of the disclosure are related to the characteristics of the pharmaceutical composition and the particular therapeutic effect to be achieve.

The principal pharmaceutical composition is compounded for convenient and effective administration in effective amounts with a suitable pharmaceutically acceptable carrier in an acceptable dosage unit. In the case of compositions containing supplementary active ingredients, the dosages are determined by reference to the usual dose and manner of administration of the said ingredients.

The pharmaceutical compositions according to the disclosure may be administered at a therapeutically effective amount either locally or systemically. As used herein, "administering a therapeutically effective amount" is intended to include methods of giving or applying a pharmaceutical composition of the disclosure to a subject that allow the composition to perform its intended therapeutic function. The therapeutically effective amounts will vary according to factors, such as the degree of infection in a subject, the age, sex, and weight of the individual. Dosage regime can be adjusted to provide the optimum therapeutic response. For example, several divided doses can be administered daily or the dose can be proportionally reduced as indicated by the exigencies of the therapeutic situation.

The disclosure provides methods for treating a subject with a cancer or suspected of having a cancer comprising administering a therapeutically effective amount of one or more prodrugs disclosed herein. A therapeutically effective amount can be measured as the amount sufficient to prevent cancer cells from dividing and growing, ultimately killing the cancer cells. Generally, the optimal dosage of prodrugs will depend upon the type and stage of the cancer and factors such as the weight, sex, and condition of the subject. Nonetheless, suitable dosages can readily be determined by an expert in the field. Typically, dosages used in vitro may provide useful guidance in the amounts useful for in situ administration of the pharmaceutical composition, and animal models may be used to determine effective dosages for treatment of specific infections. Various considerations are described, e.g., in Langer, Science, 249: 1527, (1990); Gilman et al. (eds.) (1990), each of which is herein incorporated by reference. Typically, a suitable dosage for treating a cancer with the prodrugs is 1 to 1000 mg/kg body weight, e.g., 150 to 500 mg/kg body weight. In a particular embodiment, a prodrug disclosed herein is administered at dosage of 10 mg/kg, 20 mg/kg, 30 mg/kg, 40 mg/kg, 50 mg/kg, 60 mg/kg, 70 mg/kg, 80 mg/kg, 90 mg/kg, 100 mg/kg, 110 mg/kg, 120 mg/kg, 130 mg/kg, 140 mg/kg, 150 mg/kg, 160 mg/kg, 170 mg/kg, 180 mg/kg, 190 mg/kg, 200 mg/kg, 250 mg/kg, 300 mg/kg, 350 mg/kg, 400 mg/kg, 450 mg/kg, 500 mg/kg, 550 mg/kg, 600 mg/kg, 650 mg/kg, 700 mg/kg, 750 mg/kg, 800 mg/kg, 850 mg/kg, 900 mg/kg, 950 mg/kg, 1000 mg/kg, or a range that includes or is between any two of the foregoing dosages, including fractional dosages thereof.

In a further embodiment, a prodrug of the disclosure is formulated for oral delivery. Examples of formulations for oral delivery include, but are not limited to, tablets, capsules, pills, syrups, suspensions, films, elixirs, powders, sprays, pastilles, solutions, and chewable gels. In a particular embodiment, a prodrug of the disclosure is formulated as a capsule. In a further embodiment, a capsule comprising a prodrug of the disclosure further comprises, gelatin, magnesium stearate, mannitol, titanium dioxide, and/or yellow iron oxide. In yet a further embodiment, the capsule comprising a prodrug of the disclosure is enterically coated.

The disclosure also provides a method for inhibiting the growth of a tumor or cancer by contacting the tumor cells, cancer cells or neoplastic cells with a with an inhibiting effective amount of a prodrug disclosed herein. The term "contacting" refers to exposing the cells (e.g., tumor, cancer or neoplastic cell) to an agent. Contacting can occur in vivo, for example, by administering a Prodrug of the disclosure to a subject afflicted with a tumor, cancer or neoplasm. In vivo contacting includes both parenteral as well as topical. "Inhibiting" or "inhibiting effective amount" refers to the amount of a prodrug disclosed herein that is sufficient to cause, for example, tumor, cancer or neoplastic cell death, inhibition of growth and/or migration and/or inhibition of prevention of metastasis.

Cancers in many instances become resistant to chemotherapeutic treatments, ultimately limiting their usefulness. By co-delivering one or more anticancer agents with the prodrugs disclosed herein, the cancer can be attacked at multiple levels. Accordingly, administering one or more anticancer agents with a prodrug disclosed herein can increase the effectiveness of the cancer therapy.

Accordingly, the disclosure provides a method for inhibiting a cancer and/or a neoplastic disorder by contacting or administering a prodrug of the disclosure with one or more anticancer agents to a subject who has a cancer or is at risk of having a cancer. The term "inhibiting" means preventing or ameliorating a sign or symptoms of a cancer and/or a neoplastic disorder (e.g., tumor growth, cancer cell proliferation and/or migration, cancer cell metastasis, and the like). The anticancer agents may be administered concurrently or sequentially with the prodrug. Examples, of anticancer agents that can be used with the prodrugs disclosed herein include, but are not limited to, alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and tiimethylolomelamine; acetogenins (e.g., bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; vinca alkaloids; epipodophyllotoxins; antibiotics such as the enediyne antibiotics (e.g., calicheamicin, especially calicheamicin gammaII and calicheamicin omegaII; L-asparaginase; anthracenedione substituted urea; methyl hydrazine derivatives; dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; antimetabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitiaerine; pentostatin; phenamet; pirarubicin; losoxantione; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2 2"-trichlorotiiethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® (docetaxel) (Rhone-Poulenc Rorer, Antony, France); chloranbucil; GEMZAR® (gemcitabine); 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (e.g., CPT-11); topoisomerase inhibitor RFS 2000; difluoromethylornithine (DFMO); retinoids such as retinoic acid; capecitabine; leucovorin (LV); irenotecan; adrenocortical suppressant; adrenocorticosteroids; progestins; estrogens; androgens; gonadotropin-releasing hormone analogs; and pharmaceutically acceptable salts, acids or derivatives of any of the above. Also included anticancer agents are anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON-toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASL® exemestane, formestanie, fadrozole, RIVISOR® vorozole, FEMARA® letrozole, and ARTMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Ralf and H-Ras; ribozymes such as a VEGF-A expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELLX® rmRH; antibodies such as trastuzumab and pharmaceutically acceptable salts, acids or derivatives of any of the above. In a particular embodiment, the disclosure provides for combined therapy comprising one or more Prodrugs disclosed herein used in combination with a tyrosine kinase inhibitor (TKI). Examples of protein kinase inhibitors, include but are not limited to, adavosertib, afatinib, axitinib, bosutinib, cetuximab, cobimetinib, crizotinib, cabozantinib, dasatinib, entrectinib, erdafitinib, erlotinib, fostamatinib, gefitinib, ibrutinib, imatinib, lapatinib, lenvatinib, mubritinib, nilotinib, pazopanib, pegaptanib, ruxolitinib, sorafenib, sunitinib, SU6656, vandetanib, and vemurafenib. In another embodiment, the disclosure provides for combined therapy comprising one or more Prodrugs disclosed herein used in combination with an angiogenesis inhibitor. Examples of angiogenesis inhibitors, include but are not limited to, axitinib, bevacizumab, cabozantinib, everolimus, lenalidomide, lenvatinib mesylate, pazopanib, ramucirumab, regorafenib, sorafenib, sunitinib, thalidomide, vandetanib, and Ziv-aflibercept. In another embodiment, the disclosure provides for combined therapy comprising one or more Prodrugs disclosed herein used in combination with a PARP inhibitor. Examples of PARP inhibitors, include but are not limited to, olaparib, niraparib, rucaparib, and talzoparib. The anticancer agent may be administered, by a route and in an amount commonly used therefore, simultaneously (at the same time or in the same formulation) or sequentially with a prodrug as disclosed herein. When a prodrug as disclosed herein is used contemporaneously with one or more anticancer agents, a pharmaceutical composition containing the one or more anticancer agents in addition to a prodrug disclosed herein may be utilized but is not required. Accordingly, the pharmaceutical compositions disclosed herein include those that also contain one or more anticancer agents in addition to a prodrug disclosed herein.

The disclosure also provides for use of the prodrug disclosed herein to treat subject with multiple sclerosis. As noted herein the prodrug gets converted to fingolimod when administered to a subject. Fingolimod is an FDA approved immunomodulatory drug for treating multiple sclerosis that inhibits lymphocyte egress from lymphoid tissues by down regulating sphingosine-1 phosphate receptor (S1PR). Recent studies found that fingolimod inhibits T cell activation (TCA) in a S1PR-independent manner. As such, the prodrug finds use as a treatment with subjects with multiple sclerosis.

The disclosure provides methods for treating a subject with multiple sclerosis or suspected of having multiple sclerosis comprising administering a therapeutically effective amount of one or more prodrugs disclosed herein. A therapeutically effective amount can be measured as the amount sufficient to ameliorate symptoms associated with multiple sclerosis. Generally, the optimal dosage of prodrugs will depend upon the type and stage of the cancer and factors such as the weight, sex, and condition of the subject. Nonetheless, suitable dosages can readily be determined by an expert in the field. Typically, dosages used in vitro may provide useful guidance in the amounts useful for in situ administration of the pharmaceutical composition, and animal models may be used to determine effective dosages for treatment of specific infections. Various considerations are described, e.g., in Langer, Science, 249: 1527, (1990); Gilman et al. (eds.) (1990), each of which is herein incorporated by reference. Typically, a suitable dosage for treating multiple sclerosis with the prodrugs is 0.5 mg/kg to 500 mg/kg body weight, e.g., 1 mg/kg to 50 mg/kg body weight. In a particular embodiment, a prodrug disclosed herein is administered at dosage of 0.5 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 15 mg/kg, 20 mg/kg, 25 mg/kg, 30 mg/kg, 40 mg/kg, 50 mg/kg, 60 mg/kg, 70 mg/kg, 80 mg/kg, 90 mg/kg, 100 mg/kg, 110 mg/kg, 120 mg/kg, 130 mg/kg, 140 mg/kg, 150 mg/kg, 200 mg/kg, 250 mg/kg, 300 mg/kg, 350 mg/kg, 400 mg/kg, 450 mg/kg, 500 mg/kg, or a range that includes or is between any two of the foregoing dosages, including fractional dosages thereof.

Furthermore, the prodrug can be combined with additional multiple sclerosis treatments to treat a subject in need thereof. The multiple sclerosis treatments may be administered concurrently or sequentially with the prodrug. Examples, of multiple sclerosis treatments that can be used with the prodrugs disclosed herein include, but are not limited to, beta interferons, glatiramer acetate, dimethyl fumarate, teriflunomide, siponimod, ocrelizumab, natalizumab, alemtuzumab, and mitoxantrone.

For use in the therapeutic applications described herein, kits and articles of manufacture are also described herein. Such kits can comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers can be formed from a variety of materials such as glass or plastic.

For example, the container(s) can comprise one or more prodrugs described herein, optionally in a composition or in combination with another agent as disclosed herein. The container(s) optionally have a sterile access port (for example the container can be an intravenous solution bag or a vial having a stopper pierceable by a hypodermic injection needle). Such kits optionally comprise a compound disclosed herein with an identifying description or label or instructions relating to its use in the methods described herein.

A kit will typically comprise one or more additional containers, each with one or more of various materials (such as reagents, optionally in concentrated form, and/or devices) desirable from a commercial and user standpoint for use of a compound described herein. Non-limiting examples of such materials include, but are not limited to, buffers, diluents, filters, needles, syringes; carrier, package, container, vial and/or tube labels listing contents and/or instructions for use, and package inserts with instructions for use. A set of instructions will also typically be included.

A label can be on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein. These other therapeutic agents may be used, for example, in the amounts indicated in the Physicians' Desk Reference (PDR) or as otherwise determined by one of ordinary skill in the art.

The following examples are intended to illustrate but not limit the disclosure. While they are typical of those that might be used, other procedures known to those skilled in the art may alternatively be used.

Examples

Materials. All chemicals purchased from various vendors were used as received without further purification. Fingolimod.HCl was purchased from LC Laboratories (Woburn, Mass.). Succinimidyl PEG NHS 5K (mPEG SCM 5K) was purchased from Nanocs (Boston, Mass.). Anhydrous tetrahydrofuran (THF), anhydrous ethyl acetate (EtOAc), dichloromethane (DCM), anhydrous toluene, 3 Å molecular sieves, triethylamine (TEA), and pyridinium p-toluene sulfonate (PPTS) were purchased from Acros Organics (Morris Plains, N.J.). Para-toluenesulfonic acid monohydrate (pTSA), anhydrous dimethylformamide (DMF) and dimethylsulfoxide (DMSO) were purchased from Sigma Aldrich (Milwaukee, Wis.). Fmoc-n-piperidone, anhydrous magnesium sulfate, and all cell culture materials were purchased from Fisher Scientific (Hampton, N.H.). $^1$H NMR spectra were obtained using a Bruker Advance 500 MHz NMR spectrometer (Billerica, Mass.). Electrospray mass spectra were obtained by using a Micromass LCT mass spectrometer (Milford, Mass.). For the determination of average molecular weight of mPEG SCM 5K and PEGylated prodrugs AB SCIEX MALDI TOF-TOF 5800 instruments (Framingham, Mass.) was used and samples were prepared using 2,5-dihydroxybenzoic acid (Acros Organics (Morris Plains, N.J.) as matrix material. The samples were irradiated with 349 nm of diode-pumped solid state Nd:YAG laser and detected on linear high mass positive mode. For the molecular weight analysis, Mn calculated using Data Explorer software (Applied Biosystems, Foster City, Calif.).

Synthesis: FTY-TFA (2). Fingolimod.HCl (1.00 g, 2.9 mmol) was dissolved in 150 mL of dehydrated ethanol at room temperature. Triethylamine (1.00 mL, 7.25 mmol) was added. The mixture was stirred for 25 min, followed by the addition of ethyl trifluoroacetate (0.450 mL, 3.7 mmol) and further stirring for 24 h. The solvent was removed in vacuo and the product was separated by silica gel column chromatography (EtoAc:Hex). Yield 70.6%. $^1$H NMR (600 MHz, DMSO-d$_6$, 25° C.), δ 8.05 (s, 1H), 7.08 (m, 4H), 4.85 (t, 2H), 3.69 (dd, 2H), 3.55 (m, 2H), 2.49 (m, 4H), 1.92 (m, 2H), 1.54 (m, 2H), 1.27 (m, 10H), 0.87 (t, 3H). $^{13}$C NMR (600 MHz, DMSO-d$_6$, 25° C.), 5140.03, 139.85, 128.65, 128.46, 62.16, 60.07, 36.96, 34.69, 31.55, 31.24, 31.03, 28.80, 28.64, 28.31, 22.05, 13.91 (ESI) calcd. for $C_{21}H_{32}F_3NO_3$ [M+Na]$^+$ 426.459, found 426.211.

mkFTY-TFA (3). PPTS (0.053 g, 0.213 mmol) was added to FTY-TFA (0.86 g, 2.13 mmol) in 25 mL of anhydrous THF and stirred for 10 m. Molecular sieves (5 Å) (10 g) were added and the mixture was stirred for 10 min in an ice bath, followed by the addition of 2-methoxypropene (1.22 mL, 12.7 mmol). The mixture was stirred for 2 h. The reaction was quenched with triethylamine (0.029 mL) and product was purified via extraction with DI water, dried over anhydrous MgSO$_4$. Yield 86%. $^1$H NMR (600 MHz, DMSO-d$_6$, 25° C.), δ 8.08 (s, 1H), 7.08 (m, 4H), 3.16 (q, 4H), 3.11 (s, 6H), 2.46 (m, 4H), 1.54 (m, 4H), 1.27 (m, 22H), 0.87 (t, 3H). (ESI) calcd. for $C_{29}H_{48}F_3NO_5$ [M+Na]$^+$ 570.680, found 570.472.

mkFTY (4). kFTY-TFA (3) was dissolved in 3N NaOH in 1:1 water:methanol for 6 h and product was extracted 9 times with dichloromethane. Yield 61%. $^1$H NMR (600 MHz, DMSO-d$_6$, 25° C.), δ 7.08 (m, 4H), 3.16 (q, 4H), 3.11 (s, 6H), 2.46 (m, 2H), 1.54 (m, 4H), 1.27 (m, 22H), 0.87 (t, 3H)$^{13}$C NMR (600 MHz, DMSO-d$_6$, 25° C.), 5128.18, 127.98, 99.17, 64.54, 53.53, 47.82, 37.43, 37.18, 34.74, 31.25, 31.05, 28.82, 28.65, 24.31, 24.25, 22.07, 13.94 (ESI) calcd. for $C_{27}H_{49}NO_4$ [M+Na]$^+$ 474.672, found 474.724.

Fmoc-kFTY-TFA (5). In toluene (10 mL), p-toluenesulfonic acid monohydrate (424 mg, 2.2 mmol) was heated at reflux for 1 h, while water was distilled off by condensation. FTY-TFA (700 mg, 1.7 mmol) and 4-Fmoc-piperidone (1.4 g, 5.2 mmol) were added in 10 mL of toluene, and heated to 110° C. for 6 h using a Dean-Stark trap. The solvent was removed in vacuo and the product was purified by column chromatography with eluting solvent gradient of hexane to 5:3 hexane:ethyl acetate (1% TEA to prevent hydrolysis). Yield 52%. $^1$H NMR (600 MHz, DMSO-d$_6$, 25° C.), δ 7.91 (d, 2H), 7.64 (d, 2H), 7.44 (t, 2H), 7.36 (t, 2H), 7.10 (d, 2H), 7.05 (d, 2H), 4.40 (m 2H), 4.25 (t, 1H), 4.18 (d, 2H), 3.83 (d, 2H), 3.22 (d, 2H), 2.41 (m, 2H), 1.85 (m, 4H), 1.55 (m, 4H), 1.27 (m, 10H), 0.87 (t, 3H). $^{13}$C NMR (600 MHz, DMSO-d$_6$, 25° C.), 5155.02, 144.24, 141.28, 128.15, 127.63, 125.47, 120.61, 67.04, 47.36, 36.99, 35.18, 29.32, 29.11, 20.48, 14.31 (ESI) calcd. for $C_{41}H_{49}F_3N_2O_5$ [M+Na]$^+$ 729.823, found 729.874.

kFTY-TFA (6). Fmoc-protected kFTY-TFA (0.100 g, 0.141 mmol) was dissolved in anhydrous THF (1.4 mL) and piperidine (5% v/v, 0.069 mL) was added, followed by stirring at room temperature for 24 h. Upon disappearance of starting materials as monitored by TLC, solvent was removed under reduced pressure. The crude product was dissolved in methylene chloride and purified by column chromatography using ethyl acetate containing 1% TEA. The title product was afforded as a light-yellow oil. Yield 61.18%. $^1$H NMR (600 MHz, CDCl$_3$, 25° C.), δ 7.01 (d, 2H), 6.97 (d, 2H), 6.50 (s, 1H), 3.90 (d, 2H), 3.67 (d, 2H), 2.87 (t, 2H), 2.77 (t, 2H), 2.48 (t, 2H), 2.43 (t, 2H), 1.99 (m, 2H), 1.89 (m, 2H), 1.66 (t, 2H), 1.50 (m, 2H), 1.21 (m, 10H), 0.80 (t, 3H). $^{13}$C NMR (600 MHz, DMSO-d$_6$, 25° C.), 5162.26, 156.09, 139.74, 138.57, 128.25, 127.89, 116.55, 96.51, 69.7, 62.96, 54.47, 42.45, 35.9, 35.76, 34.72, 32.41, 31.25, 31.02, 30.76, 28.82, 28.63, 27.85, 22.06, 13.94 (ESI) calcd. for $C_{26}H_{39}F_3N_2O_3$ [M+H]$^+$ 485.602, found 485.746.

kFTY (7). kFTY-TFA (100 mg, 0.2 mmol) in 6N NaOH with a minimal amount of methanol used for solubility was stirred overnight at room temperature. The product was extracted with dichloromethane 9 times and solvent was removed under a reduced pressure. The title product was obtained as a white solid. Yield 77%. $^1$H NMR (600 MHz, DMSO-d$_6$, 25° C.), δ 7.07 (d, 4H), 3.59 (d, 2H), 3.41 (d, 2H), 2.62 (m, 4H), 2.53 (m, 2H), 2.42 (m, 1H), 1.78 (m, 4H), 1.65 (m, 4H), 1.56 (m, 2H), 1.52 (t, 2H), 1.24 (m, 10H), 0.84 (t, 3H). $^{13}$C NMR (600 MHz, DMSO-d$_6$, 25° C.), 5128.35, 128.01, 48.10, 37.14, 34.73, 31.25, 31.04, 28.82, 28.65, 27.87, 22.07, 13.94 (ESI) calcd. for $C_{24}H_{40}N_2O_2$ [M+H]$^+$ 389.594, found 389.688.

FTY-k-PEG (8). kFTY-TFA (75 mg, 0.155 mmol) was dissolved in anhydrous dichloromethane (2 mL) and mixed with trimethylamine (432 µL, 3.1 mmol), followed by stirring for 5 min. After mPEG SCM 5K (462 mg, 0.093 mmol) was added and stirred overnight, the crude product was obtained as white solid. Yield 100%. MALDI-TOF Average M$_n$=5628.7 g/mol (mPEG SCM 5K average M$_n$=5171.1 g/mol). Crude TFA-FTY-k-PEG (150 mg, 0.155 mmol) obtained in the prior reaction without further purification was dissolved in 6N NaOH (2 mL) and stirred for 24 h, then diluted to 50 mL using deionized water and dialyzed overnight using a 2,000 MWCO dialysis cassette (Fisher Scientific, Hampton, N.H.). The title product was lyophilized to yield a white powder. Yield 77%. MALDI-TOF Average M$_n$=5496.3 g/mol.

FTY-k-PEG hydrolysis and fingolimod release. FTY-k-PEG (14 mg) was dissolved separately in 1 mL of deuterated acetate buffer (pH 5.0) and 1 mL deuterated Tris-HCL buffer (pH 7.4) in $D_2O$ and shaken at 37° C. for 48 hours. $^1H$ NMR spectra were taken at 0, 6, 28, and 48 h and hydrolysis rate determined by integration of the peak at 2.23 ppm as it shifted to 1.91 ppm. Half-life was calculated using the Arrhenius equation, $t_{1/2}=\ln(k)/2$.

Cell culture. Murine IL-3-dependent proB-cell lymphoid FL5.12 cells and FL5.12/BCR-Abl p190 cells were obtained by gift. FL5.12/p190 cells were transduced to express firefly luciferase by lentiviral vectors purchased from Capital Bioscience (Gaithersberg, Md.). FL5.12/p190 and luciferase-expressing FL5.12/p190 cells (FL5.12/p190/Luc cells) were maintained at 250,000-800,000 cells/mL in RPMI 1640 media containing 10% (v/v) FBS and 1% (v/v) streptomycin-penicillin. FL5.12 cells were cultured in the same media supplemented with 5 ng/mL IL3. All cells were cultured at 37° C. with 5% $CO_2$ and 100% humidity.

Cell viability. FL5.12 and FL5.12/p190 cells were seeded in a 48-well plate at a density of $4.0\times10^4$ cells/well with or without IL-3 (5 ng/mL) (Thermo Fisher, Waltham, Mass.). After incubation in varying concentrations of fingolimod and FTY-prodrugs for 24 h and rinsed with PBS, the cells were counted by flow cytometry (Guava Technologies, Hayward, Calif.) using Guava ViaCount Reagent (Guava Technologies, Hayward, Calif.) according to the manufacturer's recommended protocols.

Nutrient transporter expression. Surface 4F2hc expression was measured using phycoerythrin (PE)-conjugated rat anti-mouse 4F2hc antibody (BD Pharmingen, San Diego, Calif.); analysis by flow cyomery was restricted to viable cells. PE-conjugated mouse IgG1, k (BD Pharmingen) was used as an isotype control. Cells were analyzed on a BD LSR II flow cytometer (BD Biosciences, San Jose, Calif.) and with FlowJo software (Treestar, Ashland, Oreg.).

Heart rate. Male C57BL/6 mice age 4-6 months were surgically implanted with DSI TA-ETAF20 electrocardiographic telemetry devices (Data Sciences International, St. Paul, Minn.) in the mouse's abdominal cavity with biopotential leads sutured in place in the chest wall. The electrocardiographic data was collected and recorded using the PhysioTel telemetry system and Dataquest A.R.T 4.0 software (Data Sciences International). Mice were permitted two week-long recovery after surgery before initiation of baseline telemetry recordings. Heart rate was calculated from ECG data taken in the freely moving, conscious mice. Mice (n=3) were intraperitoneally treated with a single dose of vehicle (0.9% saline or 20% acidified DMSO in 0.9% saline), 10 mg/kg fingolimod, or 155 mg/kg FTY-k-PEG, and heart rate was continuously monitored for 10 h. Mice were rested for two weeks at which point the experiment was repeated with the mice assigned to the alternate group. These experiments were performed as reported in Chen et al. (*ACS chemical biology* 11(2):409-414 (2016)), in accordance with all national or local guidelines and regulations and were approved by the UCI Institutional Animal Care and Use Committee (IACUC).

Lymphocyte sequestration. Female 8-24 week old C57BL6 mice were intraperitoneally injected with vehicle (0.9% saline or 20% acidified DMSO in 0.9% saline), 10 mg/kg (32 μmol/kg) fingolimod, or 155 mg/kg FTY-k-PEG (32 μmol/kg). After 12 h, blood was collected from the retro-orbital sinus under ketamine/xylazine anesthesia. Whole blood (10 μL) was added to 190 μL of ACK red blood cell lysis buffer, the mixture was incubated at ambient temperature for 3-5 min at 37° C., and the white blood cells were recovered by centrifugation. Nucleated cells ($Hoechst_{33342}$-positive) were counted using a hemocytometer to obtain the white blood cell count. Separately, 50 μL of whole blood was added to 1 mL of ACK red blood cell lysis buffer and incubated for 3-5 min at RT. Cells were washed with 2% fetal calf serum (FCS, Atlanta Biologicals (Flowery Branch, Ga.) in PBS with 0.05% NaN3 (Sigma Aldrich (Milwaukee, Wis.)) and red blood cell lysis was repeated. Tubes were decanted and resuspended in 100 μL of 10% FCS in PBS with 0.05% NaN3 and directly conjugated antibodies against B220, CD4, or CD8 (all from Biolegend, San Diego, Calif.) for 30 min on ice. Cells were analyzed on a BD LSR II flow cytometer; the analysis was restricted to live cells (DAPI-negative).

In vivo bioluminescence imaging. In an immunocompetent syngeneic model, 6-7 weeks old Balb/c female mice were intravenously injected with Ph+FL5.12/p190/Luc cells ($1.0\times10^5$ cells per mouse) in the tail vein. After 5 days, the mice received daily i.p. injections of fingolimod, FTY-k-PEG, FTY-PEG (all at a dose of 32 μmol/kg) or PBS for 5 days (n=5). Mice were placed under anesthesia using isoflurane (Patterson Veterinary, Greeley, Colo.) and interperitoneally injected with 120 mg/kg of synthetic firefly luciferin (Promega, Madison, Wis.) in PBS at a concentration of 20 mg/mL immediately prior to bioluminescence imaging with an IVIS Lumina system (Caliper Life Sciences, Hopkinton, Mass.) for 4 min. Mice were under anesthesia for the entire duration of imaging and bioluminescence signal intensities in mice were quantified using Living Image 3.2 software associated with the imaging system.

DNAge® (epigenetic aging clock) analysis. Blood samples (100 μL) were collected in triplicate from healthy female BALB/c mice treated as described above. Upon immediate preservation in DNA/RNA Shield™ (Zymo Research, Irvine, Calif.), genomic DNA was purified using Quick-DNA Plus Kit (Zymo Research) as instructed by the manufacturer. Sample library preparation and data analysis for mouse DNAge® (epigenetics aging clock) were performed by service provider (Zymo Research). Briefly, genomic DNA (200 ng) was bisulfite-converted using EZ DNA Methylation_Lightning™ Kit (Zymo Research). Bisulfite-converted DNA libraries for targeted bisulfite sequencing platform, called SWARM® (Simplified Whole-panel Amplification Reaction Method), were sequenced on a HiSeq 1500 sequencer for >1,000× coverage. Sequence reads were identified using Illumina base calling software (San Diego, Calif.) and aligned to the reference genome using Bismark, an aligner optimized for bisulfite sequence data and methylation calling. The methylation level of each sampled cytosine was estimated as the number of reads reporting a C, divided by the total number of reads reporting a C or T. DNA methylation levels of >500 age-related CpG loci were used for age prediction using Zymo Research's proprietary human DNAge® algorithms:

A penalized regression model's coefficients $b_0$, $b_1$, $b_n$ relate to transformed age as follow:

$$F(\text{chronological age})=b_0+b_1 CpG_1+\ldots+b_n CpG_n+\text{error}$$

DNAge™ is estimated as follow:

$$\text{DNAge}^{\text{TM}}=F(b_0+b_1 CpG_1+\ldots+b_n CpG_n)^{-1}$$

Statistical analysis. All data collected in duplicate or triplicate and represented as mean±standard deviation. Statistical analysis was performed with Student's t Test with statistical significance at p-values lower than 0.05.

Figure 2:
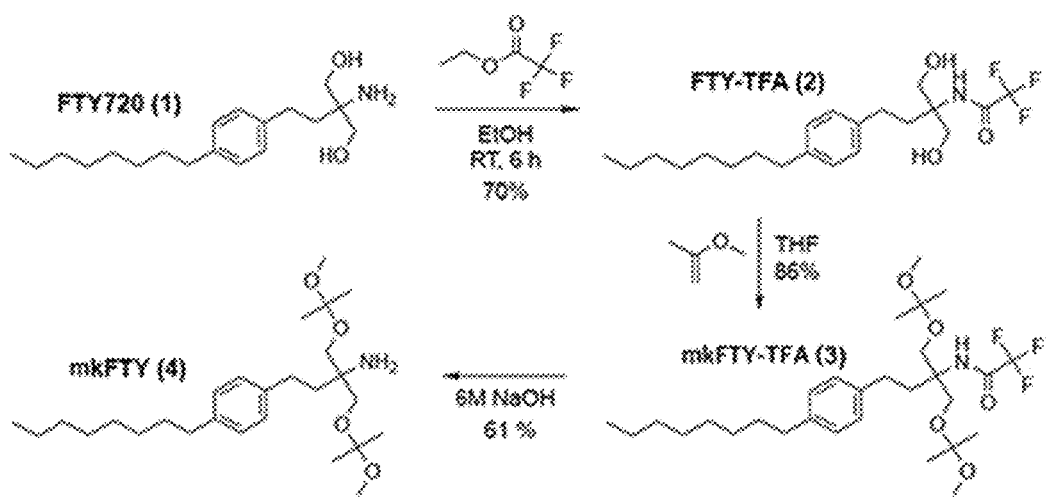
FIG. 2 provides a synthesis scheme for methyl ketal FTY (mkFTY) using 2-methoxypropene.
Figure 3:
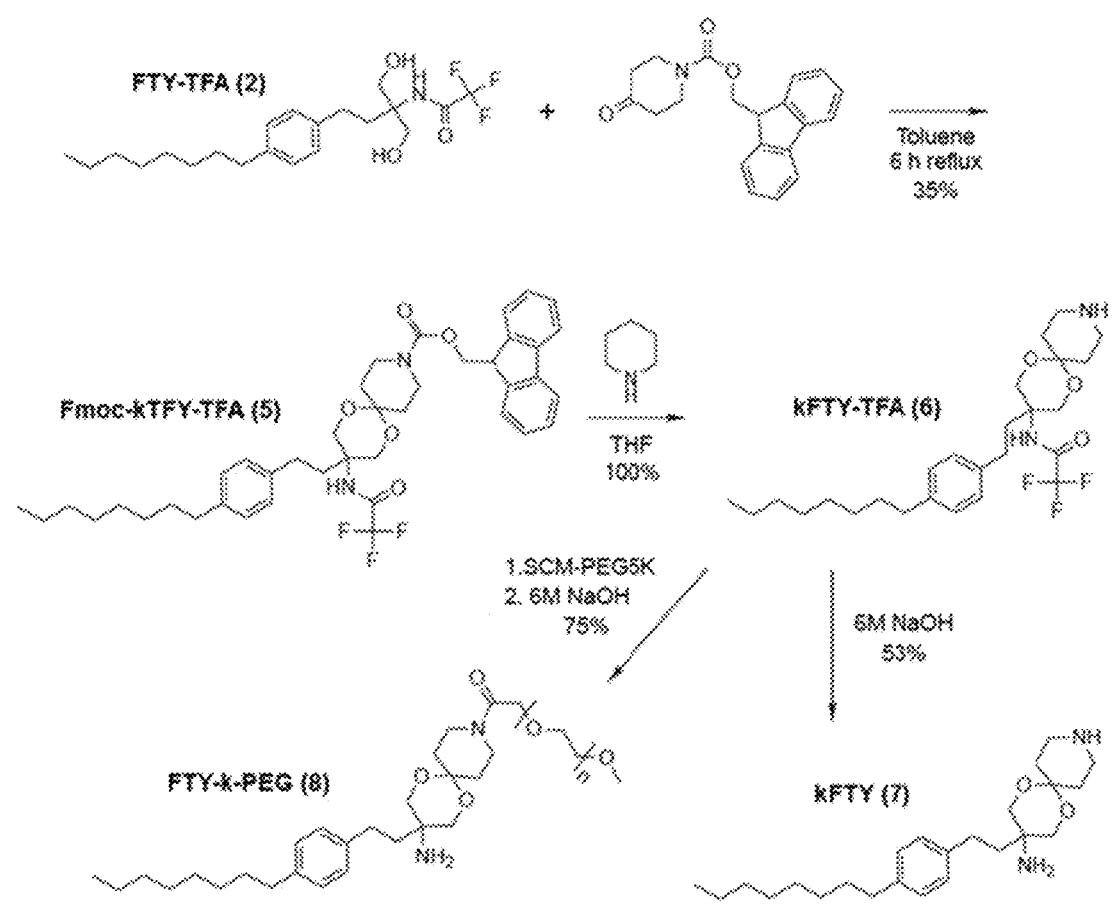
FIG. 3 provides a synthesis scheme for kFTY and FTY-k-PEG.
Figure 4:
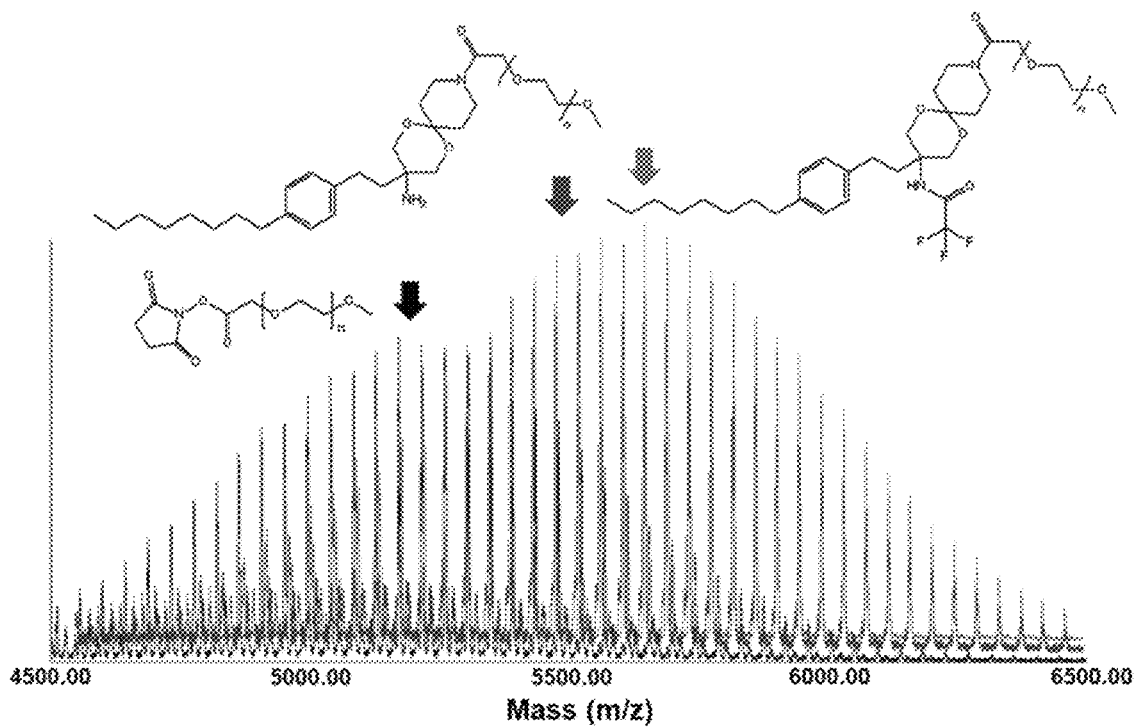
FIG. 4 confirms the PEGylation and TFA-deprotection of FTY-k-PEG by MALDI-TOF. MALDI-TOF spectra for SCM-PEG 5K, TFA-FTY-k-PEG, and FTY-k-PEG, arrow in corresponding color to demonstrate shift of average molecular weight from 5171 (SCM-PEG 5K [left arrow]) to 5628 (TFA-FTY-k-PEG [right arrow]) to 5496 (FTY-k-PEG [middle arrow]).

Design and synthesis of FTY-k-PEG. Acetals (ketals) were chosen for their structural versatility, facile synthesis, and tunable cleavability under mildly acidic conditions. The endosomal pH of ~5.0 is an excellent intracellular trigger for drug release from acid-labile drug conjugates. Initial synthetic methodology utilized 2-methoxypropene to generate methyl ketal-functionalized fingolimod (mkFTY) (see FIG. 2). The addition of hydrophobic methyl groups and loss of —OH hydrogen bonding, however, resulted in loss of water solubility. To retain the ketal moiety while increasing solubility of the prodrug, N-Fmoc piperidone was used to generate a cyclic ketal in kFTY (7) (see FIG. 3), eliminating the hydrophobic methyl groups and incorporating a secondary amine as a functional handle for further conjugation. The ketal formation was achieved using azeotropic distillation by which constant removal of water efficiently drives the reaction to completion. Although kFTY had increased water solubility compared to mkFTY, it was not readily soluble over concentrations of 10 mM. To further increase water solubility, kFTY was conjugated to succinimidyl carboxyl methyl ester polyethylene glycol (SCM-PEG 5 k) prior to trifluoroacetamide (TFA)-deprotection to produce FTY-k-PEG (8). FTY-k-PEG was analyzed by MALDI-TOF to confirm PEGylation and TFA-deprotection (see FIG. 4). Average molecular weight of SCM-PEG 5K shifted by 479 Da after conjugation with kFTY-TFA (6) (MW 484.59 g/mol), and analysis of FTY-k-PEG (8) demonstrated a decrease in average molecular weight correlating to the loss of TFA (MW 97.02 g/mol). The synthetic methodology used in this synthesis proved to be straightforward and high-yielding, and utilizes low-cost, commercially available materials to further increase translational value. Other macromolecules may be used for conjugation, and a plethora of stimuli-responsive linkers may be explored to further enhance the specificity and safety of an FTY prodrug. The acid-cleavable ketal linkage can be replaced by other moieties responsive to intrinsic environmental stimuli (redox, pH, etc.), external stimuli (heat, ultrasound, photo-irradiation, electrochemical, magnetic, etc.), or specific biological processes (enzymatic cleavage, ion chelation, etc.), depending the molecular structure of a drug and the stimuli to be utilized for target indication. In addition, a variety of macromolecules can also be used in lieu of PEG, including polysaccharides (i.e., hyaluronic acids), peptides, and various synthetic polymers for improved water-solubility, extended circulation, avoided premature activation, nanoparticle formulation, theranostic applications, combating resistance, and specific targeting. The versatility of the secondary amine on kFTY would allow development of novel combination therapy by conjugating another agent (e.g., drug and contrast agent) to further enhance its anticancer properties and combined imaging and therapy.

Figure 6A:
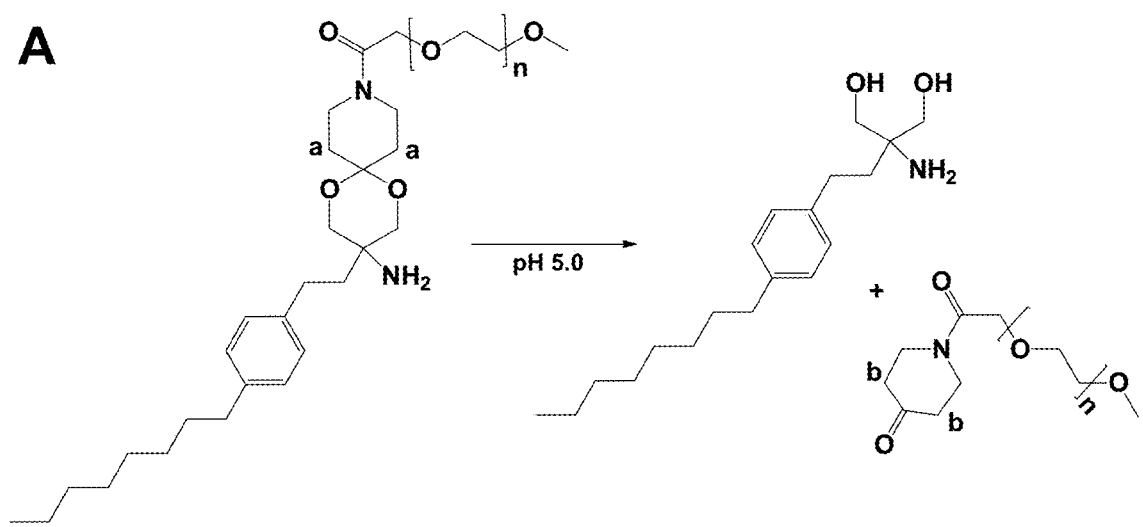
FIG. 6A-C shows that FTY-k-PEG efficiently hydrolyzes at a mildly acidic pH. (A) Chemical structures of FTY-k-PEG hydrolysis; (B) $^1$H-NMR spectra of FTY-k-PEG 10 mM deuterated acetate buffer pH 5.0 at 0, 6, 28, and 48 h timepoints; (C) hydrolysis rate was determined by the peak shift from 2.23 ppm to 1.91 ppm that correlates to the protons on the α-carbon of piperidone FIG. 7A-B demonstrates FTY-k-PEG down-regulates nutrient transporter 4f2hc. (A) FL5.12 cells were treated with either fingolimod, FTY-k-PEG or PBS for 3 h and surface 4f2hc expression was analyzed by flow cytometry; (B) Cell viability was assayed after 24 h treatment with PBS, fingolimod, and FTY-k-PEG in BCR-Abl p190-expressing FL5.12 cells. (n=3)
Figure 6B:
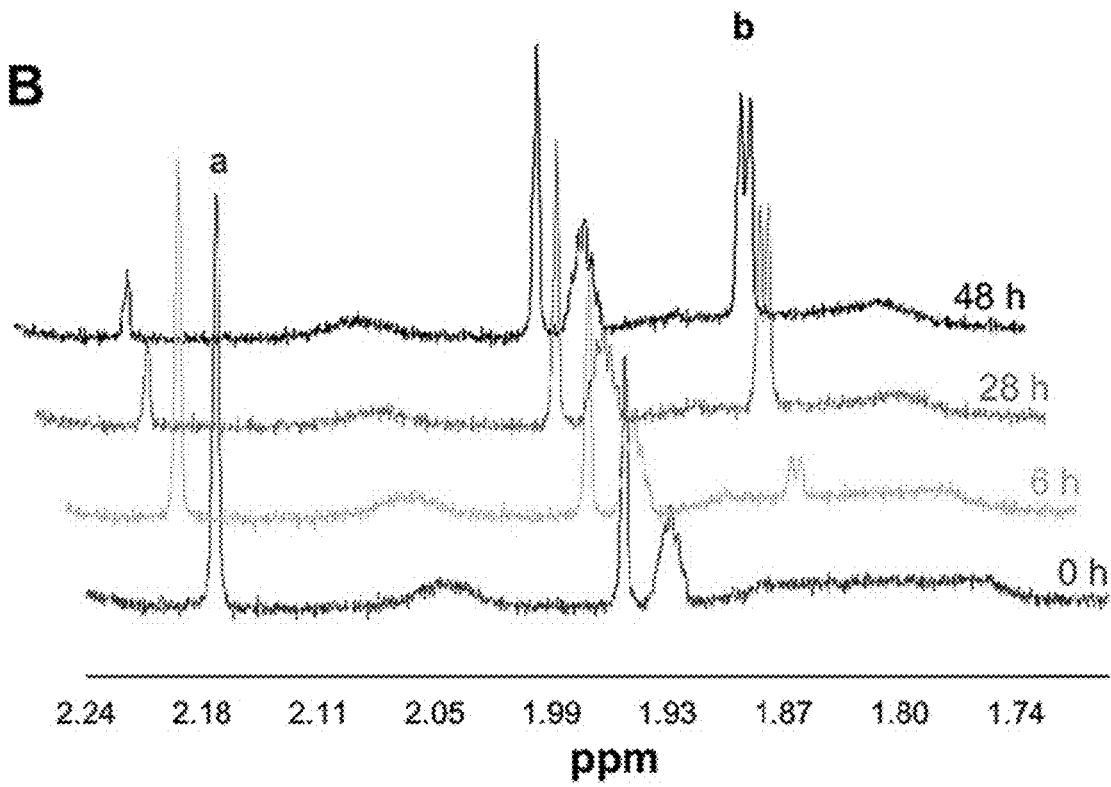
Figure 6C:
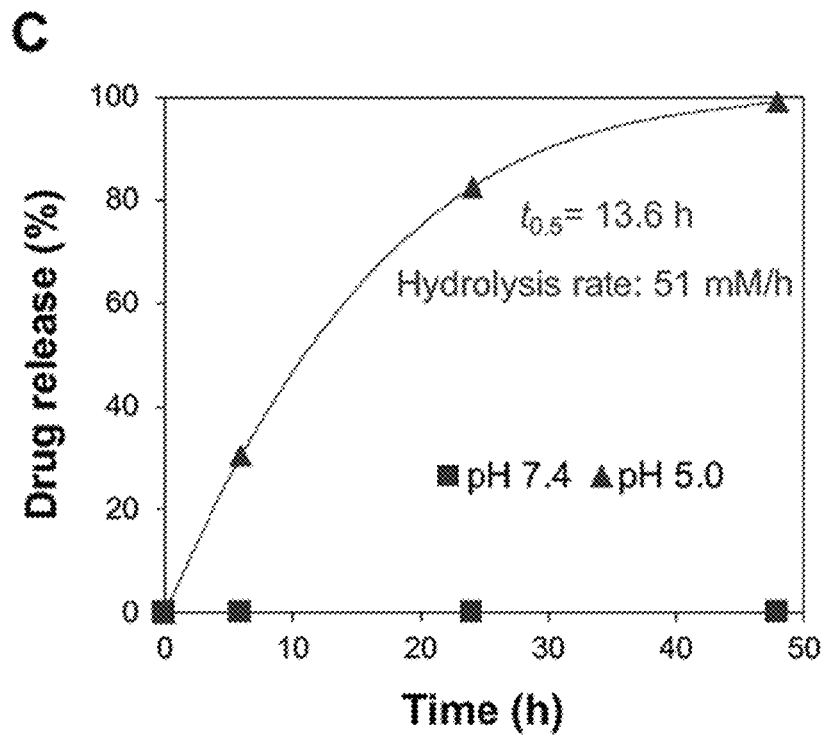

Triggered release of fingolimod from FTY-k-PEG under mildly acidic conditions. To assess the rate of drug release and demonstrate selective release under mildly acidic conditions, FTY-k-PEG was incubated at 37° C. in 10 mM deuterated acetate and tris buffers at pH 5.0 and 7.4, respectively, over the course of two days. The samples were analyzed by $^1$H-NMR taken at 0, 6, 28, and 48 h (see FIG. 6), and rate was determined by the peak at 2.23 ppm shifting to 1.91 ppm, correlating to the α-carbon protons as piperidone re-emerged. The spectra of FTY-k-PEG indicated that fingolimod was readily released at pH 5.0 (>80% after 28 h at a rate of 51 mM/h), while no detectable hydrolysis was observed at a physiological pH of 7.4 for few days. This suggests that FTY-k-PEG would be shielded from rapid phosphorylation during circulation and remain inactive toward S1PRs on off-target cells such as cardiomyocytes and lymphocytes, thus incapable of inducing onset bradycardia and lymphopenia. The drug release ratio at pH 5.0 to 7.4 was significantly higher than those using similar ketal chemistry. This might be attributed to the hydrophobic molecular environment of cyclic ketal at a neutral pH that dramatically changes to hydrophilic upon the protonation of the proximate amine at an acidic pH, greatly facilitating acid-hydrolysis. The very slow hydrolysis of FTY-k-PEG at a neutral pH also implies reasonably long-term stability in saline, particularly under low temperature storage conditions, in contrast to free fingolimod which requires daily fresh preparation.

Further studies in solid tumor cancer models are warranted since tumor extracellular environment exhibits mildly acidic conditions with pH found as low as 5.7, a distinguishing phenotype often exploited for enhanced targeting. Considering the dramatically triggered release of fingolimod from FTY-k-PEG at pH 5.0, in contrast to no measurable release at pH 7.4, the drug release in the tumor environment is speculated to be elevated compared to other tissues/organs.

Figure 5:
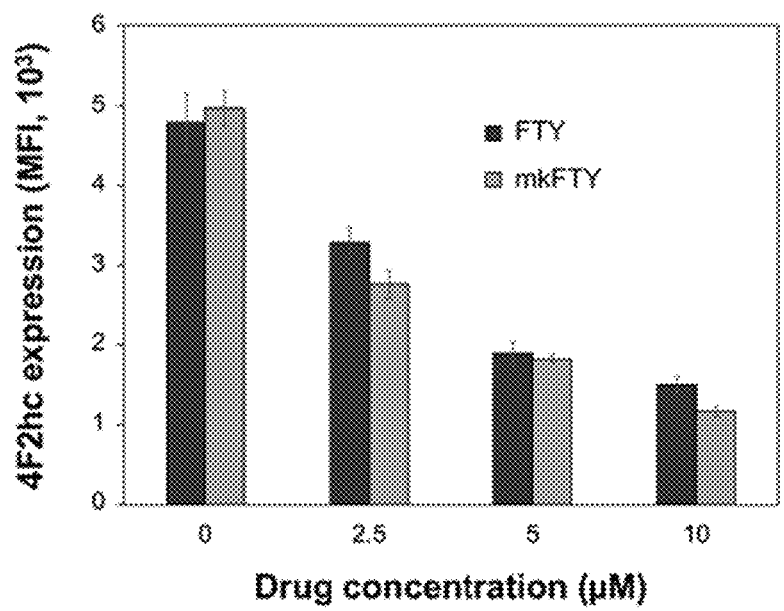
FIG. 5 demonstrates that mkFTY downregulates nutrient transporter 4f2hc in vitro. FL5.12 cells were treated with either fingolimod, kFTY or PBS for 3 hours, and surface 4f2hc expression was analyzed by flow cytometry.
Figure 7A:
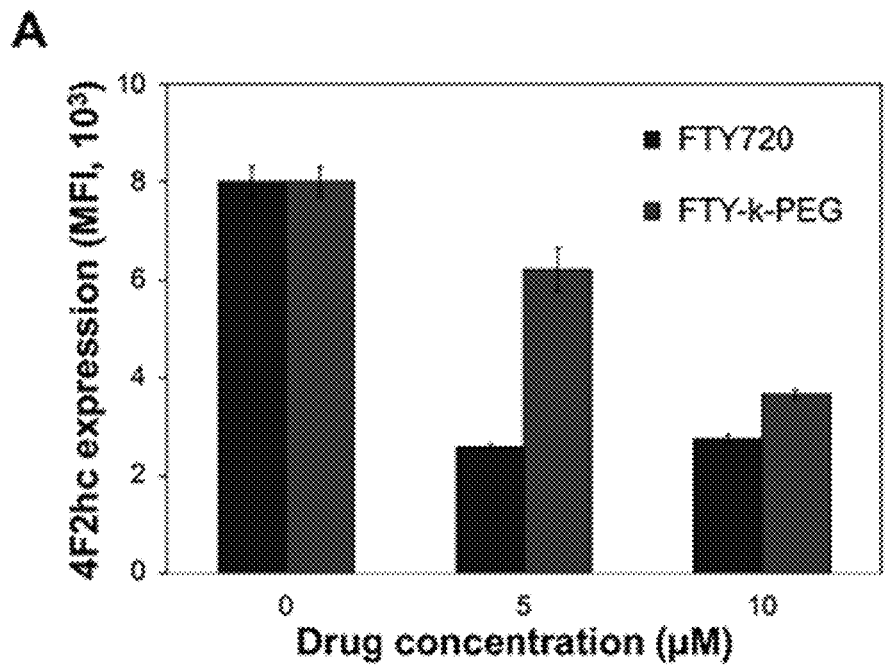
Figure 7B:
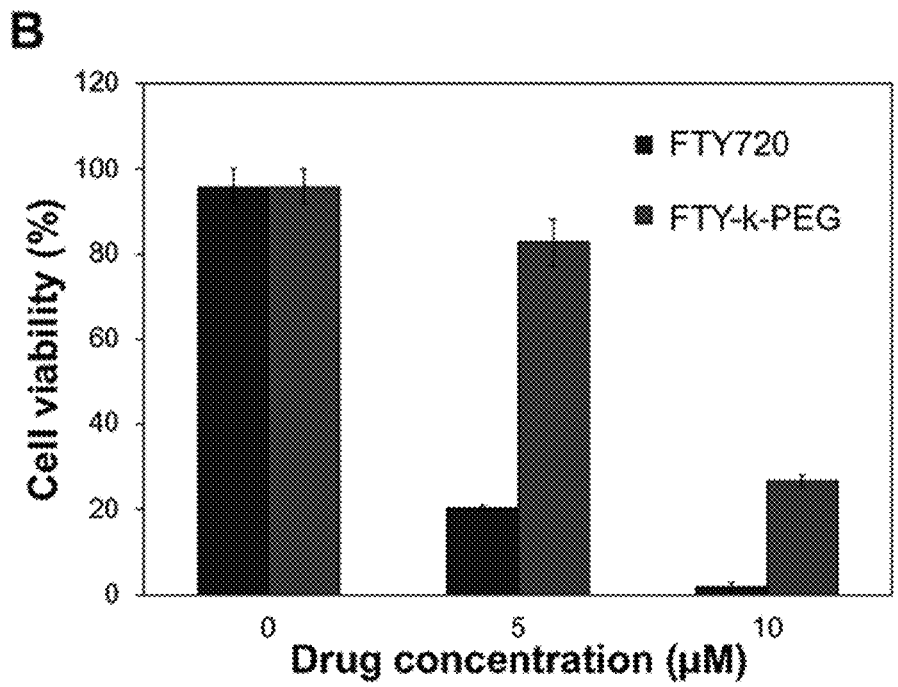
Figure 8A:
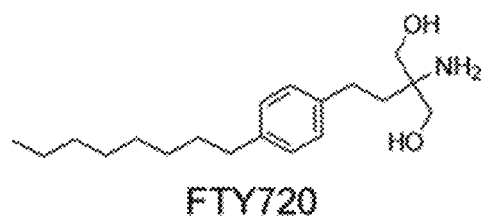
FIG. 8A-C demonstrates that FTY-k-PEG has selective acid-sensitivity and in vitro efficacy. Fingolimod (A), FTY-k-PEG (B), and FTYPEG (C) were incubated overnight in buffers of pH 5.0 (solid) and pH 7.4 (outline), and BCR-Abl p190 expressing FL5.12 cells were subsequently treated and assessed for viability after 24 hours. (n=3)
Figure 8A:
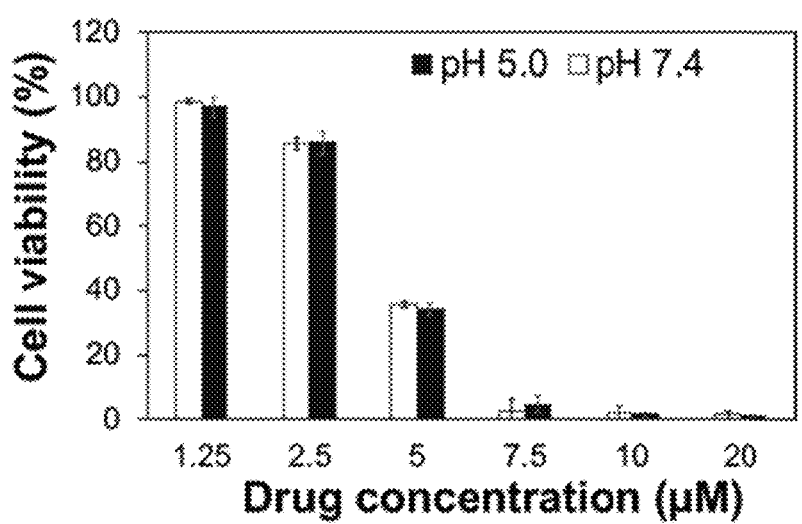
Figure 8B:
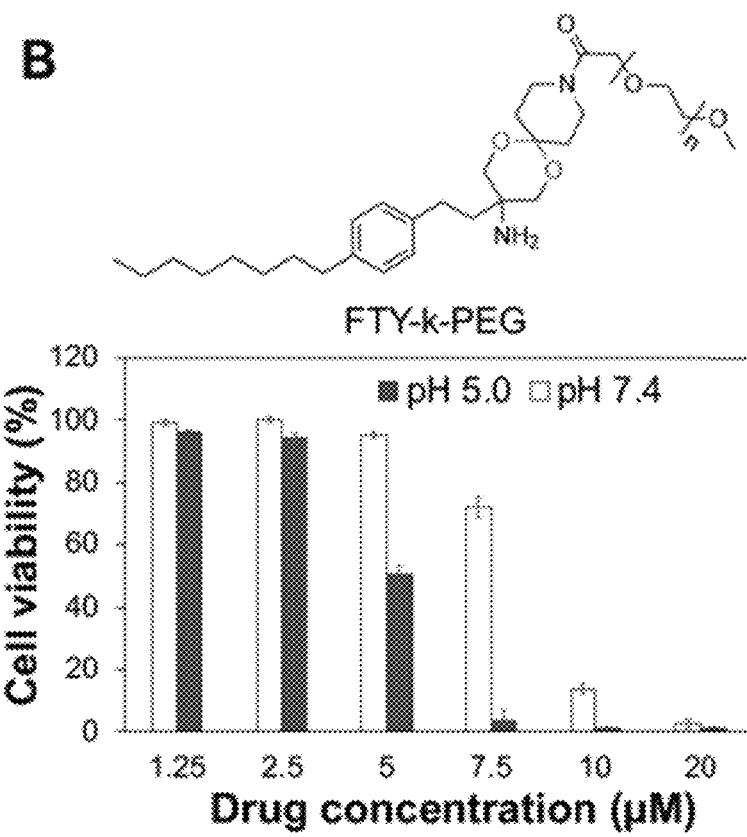
Figure 8C:
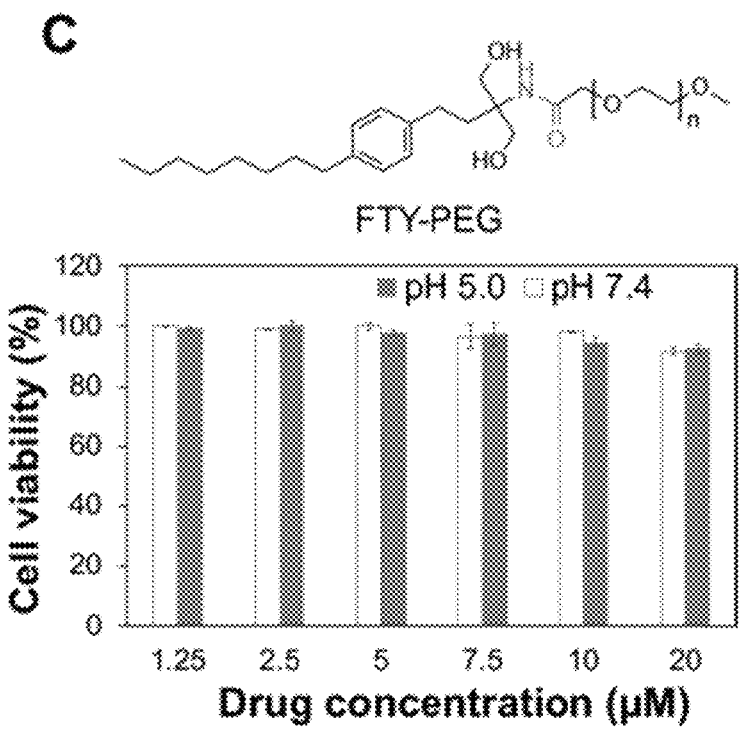
Figure 9:
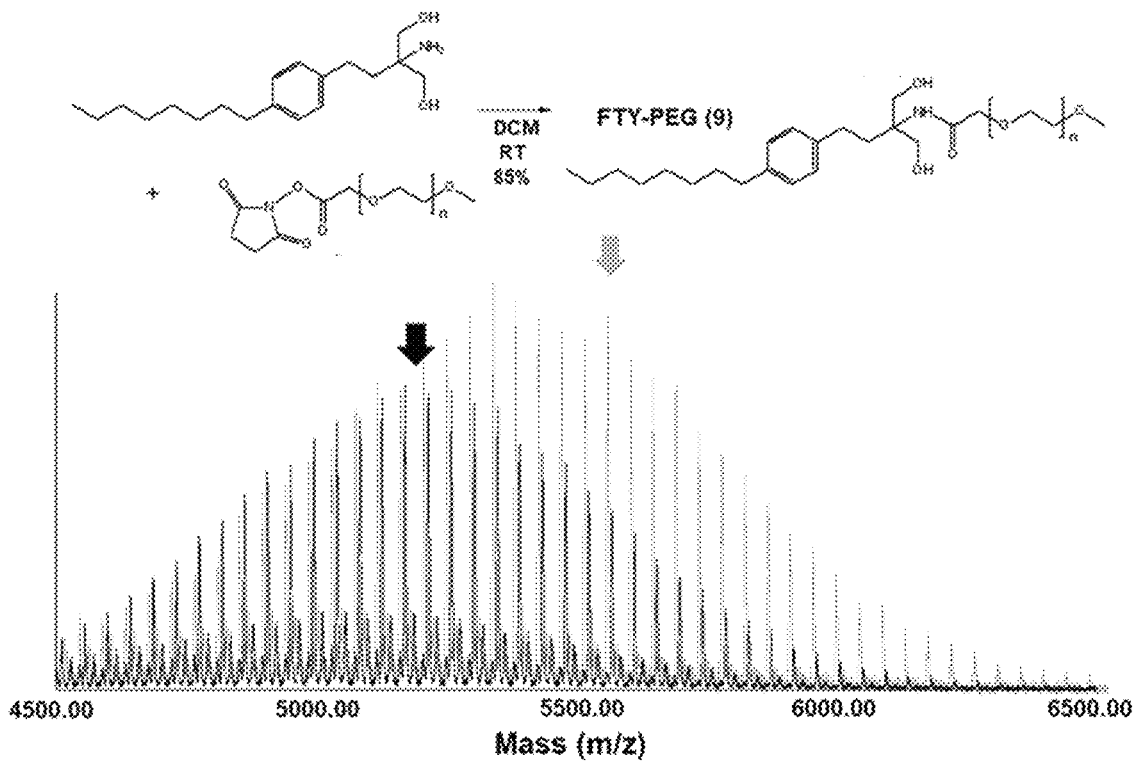
FIG. 9 confirms the synthesis of non-acid degradable FTYPEG via amide bond coupling and MALDI-TOF spectra demonstrating shift in average molecular weight from 5171 (SCM-PEG 5K [left arrow]) to 5320 (FTY-PEG [right arrow]) after conjugation.

Eradication of cancer cells by FTY-k-PEG via down-regulated nutrient transporter proteins. Fingolimod is known to effectively inhibit cancer progression via down-regulation of key nutrient transporters, selectively starving cancer cells to death. mkFTY and FTY-k-PEG were analyzed for affecting the viability and down-regulation of nutrient transporter associated protein 4F2hc in BCR-Abl p190-expressing FL5.12 murine haemopoietic cells, known to have high expression of nutrient transporters. mkFTY demonstrated nearly identical efficacy to fingolimod in nutrient transporter down-regulation, confirming no loss of function after blocking hydroxyl groups by methyl ketal groups (See FIG. 5). FTY-k-PEG decreased expression of the amino acid transporter associated protein 4f2hc albeit at a reduced efficacy than that of fingolimod, and had reduced efficacy for 24 h cell viability compared to fingolimod (se FIG. 7), possibly attributed to relatively inefficient cellular uptake of the PEGylated prodrug than the free drug and slower acid-hydrolysis of cyclic ketal than methyl ketal. To confirm active drug was released selectively upon acid-hydrolysis, drugs were incubated in buffers of pH 7.4 and pH 5.0 prior to incubation with the cells (see FIG. 8). Fingolimod was pre-incubated in the same buffers to rule out the possibility that the buffers would affect drug's activity or contribute to cell apoptosis. A non-acid-cleavable, PEGylated prodrug of fingolimod, FTY-PEG, was also synthesized by conjugating SCM-PEG 5 k to the free amine of fingolimod via amide bond (see FIG. 9), known to be extremely stable and hydrolyze only under harsh conditions or enzymatic cleavage.

As expected, FTY-PEG had no effect on cell viability, indicating no release of fingolimod. FTY-k-PEG pre-incubated at pH 7.4 yielded significant decrease in efficacy compared to fingolimod, while near identical efficacy to fingolimod is observed for FTY-k-PEG pre-incubated at pH 5.0. This demonstrates the acid-transforming nature of FTY-k-PEG and confirms its capability of releasing active drug under mildly acidic conditions. The cells were cultured in standard media where glucose concentration is not a limiting factor. The hypoglycemic microenvironment of tumors may further enhance the metabolic stress induced by released fingolimod. The apoptotic effect of fingolimod is affected by nutrient transporter levels of cancer cells and further studies would provide new insights in developing drugs for metabolic-dependent targeted therapy for each cancer type.

Figure 10A:
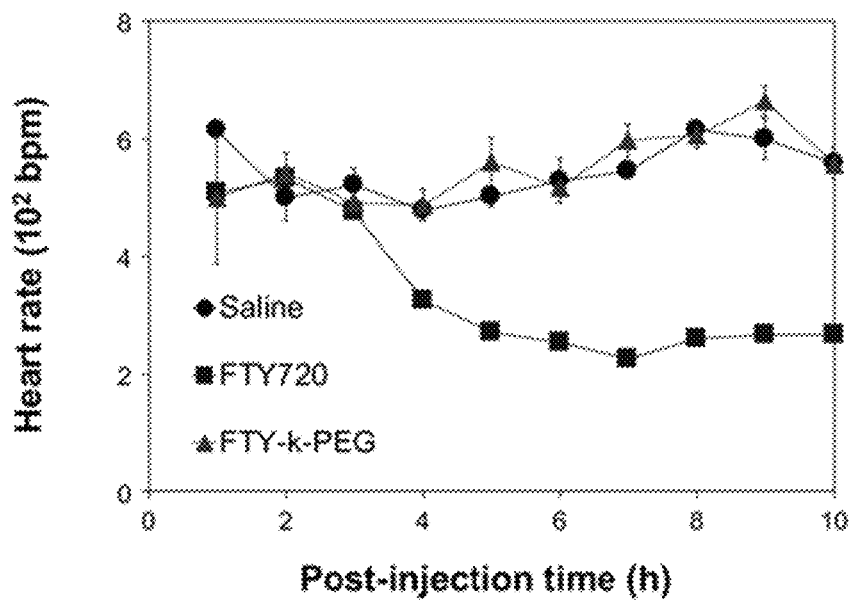
FIG. 10A-B shows that FTY-k-PEG avoids bradycardia and lymphopenia. (A) Heart rate was monitored for 10 h in freely moving, conscious C57/BL6 mice after i.p. administration of fingolimod, FTY-k-PEG, or saline; (B) C57/BL6 mice were injected with fingolimod, FTY-k-PEG, or saline, and blood was collected 12 h post-injection and analyzed for lymphocytes. (n=3)
Figure 10B:
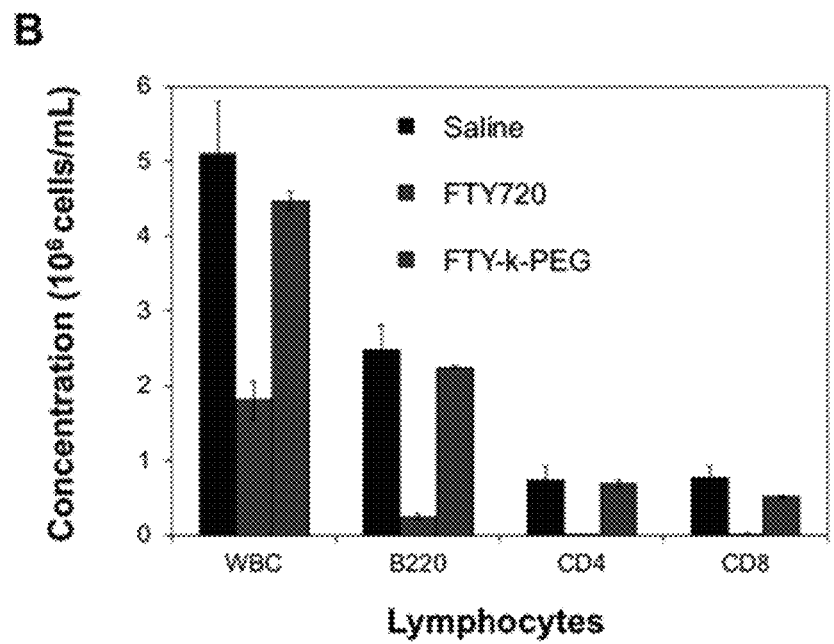
Figure 11:
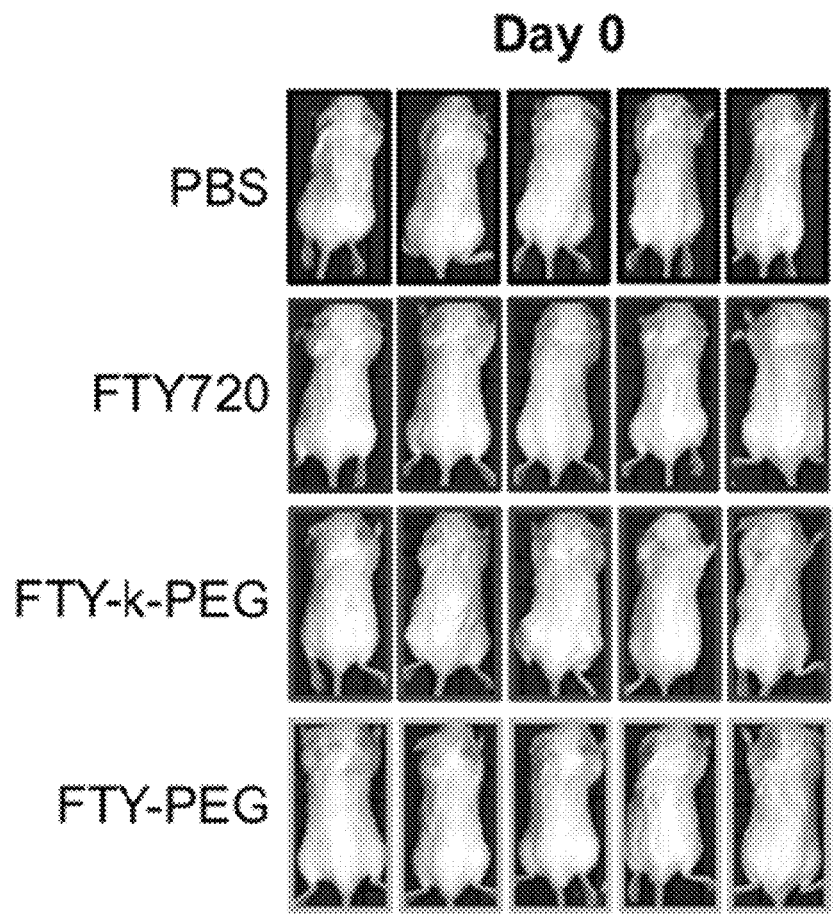
FIG. 11 presents the results of in vivo studies with FTY-k-PEG, and FTY-PEG. Mice were injected with FL5.12/BCR-Abl p190 luciferase-expressing cells, and leukemic expansion of cells was assessed by i.p. administration of synthetic firefly luciferin (120 mg/kg) and subsequent bioluminescence imaging taken on Day 0 of treatment with either PBS, fingolimod, acid-degradable FTY-k-PEG, and FTY-PEG.

Avoided bradycardia and lymphopenia in vivo by FTY-k-PEG. To test whether FTY-k-PEG avoids bradycardia, C57BL/6 mice were surgically implanted with an electrocardiographic telemetry device and heart rate was calculated from ECG data taken in the freely moving, conscious mice after intraperitoneal (i.p.) injection of saline, fingolimod, or acid-cleavable FTY-k-PEG (see FIG. 10A). Unmodified fingolimod clearly induces bradycardia, reducing heart rate by 50%, while FTY-k-PEG maintains normal heart rate, demonstrating that FTY-k-PEG fails to trigger bradycardia. To assess the effect of FTY-k-PEG on induction of lymphopenia, the numbers of circulating B and T lymphocytes were evaluated 12 h after i.p, injection of fingolimod, FTY-k-PEG, and saline in C57BL/6 mice (see FIG. 10B). Fingolimod-induced lymphopenia was evident with nearly 60% reduction of lymphocytes, compared to that in saline or FTY-k-PEG-injected mice. These results suggest the safe administration of FTY-k-PEG at an anti-neoplastic dose of 155 mg/kg (10 mg/kg equivalent fingolimod) without inducing the adverse effects associated with free fingolimod.

Limited dosing of a chemotherapeutic agent due to adverse side effects is a significant barrier to accomplishing efficient therapy for cancer, often resulting in relapse. The failure of FTY-k-PEG to trigger bradycardia and lymphopenia in vivo indicates a possibility of high-dose chemotherapy. In addition, further studies on interactions of S1PRs with fingolimod vs. FTY-k-PEG would elucidate biochemical understanding at a molecular level. The work presented herein provide a novel approach to prodrug-engineering by selectively preventing specific adverse effects through chemical modification, in contrast to many prodrugs aiming to avoid systemic side effects using a global approach. By assessing specific adverse events and the molecular mechanisms which cause them, the prodrug formulation may be fine-tuned to avoid such interactions. This concept could be applied to a multitude of cancer therapeutics to help decrease toxicity by evaluating detrimental side effects on a molecular level and designing prodrug moieties to prevent these unwanted effects.

Figure 12A:
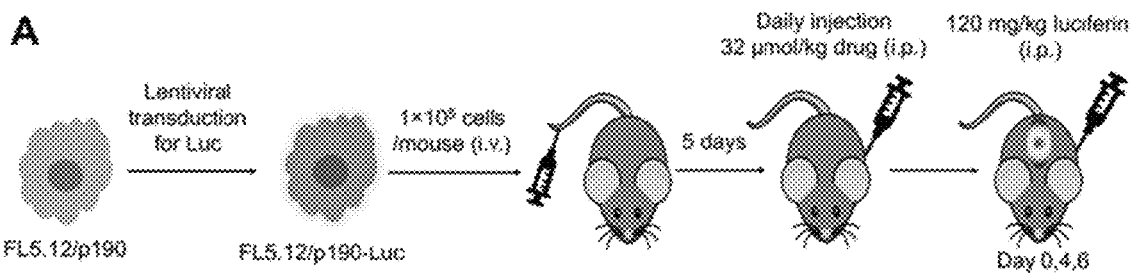
FIG. 12A-D demonstrates that FTY-k-PEG maintained anti-leukemic effect in vivo. (A) Experimental workflow for cell transduction to express luciferase, cell administration to mice, treatment and bioluminescent analysis. (B, C) Quantification of bioluminescence after mice were injected with FL5.12/p190 luciferase-expressing cells, and subsequently treated with either fingolimod, PBS, FTY-PEG or FTY-k-PEG (32 μmol/kg) for 4 and 6 days. (D) Bioluminescent images of each group on day 4 (top row) and day 6 (bottom row) post-first treatment. p<0.05, *p<0.01.
Figure 12B:
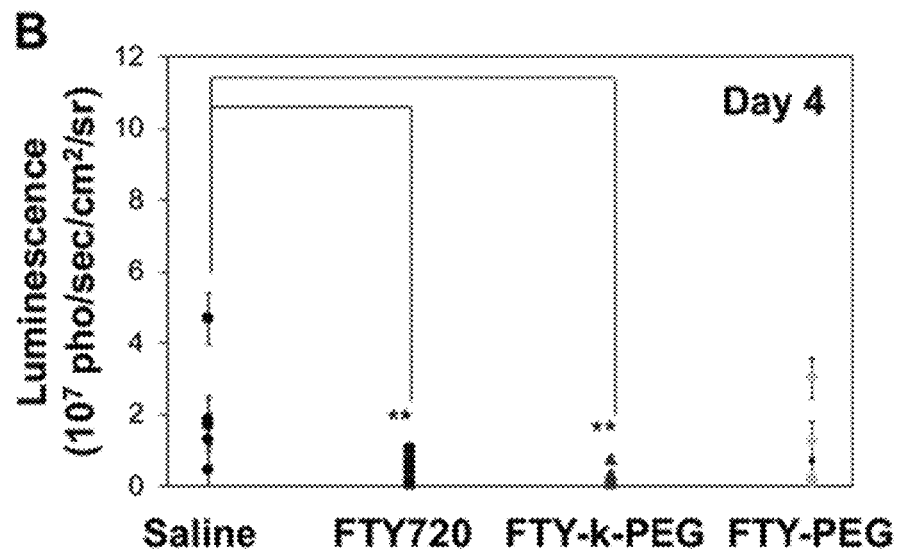
Figure 12C:
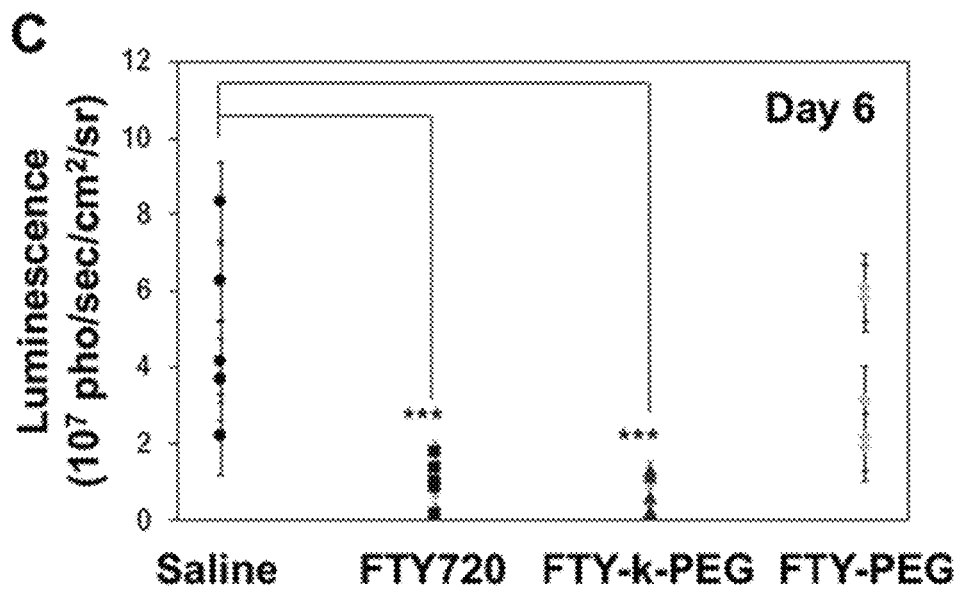
Figure 12D:
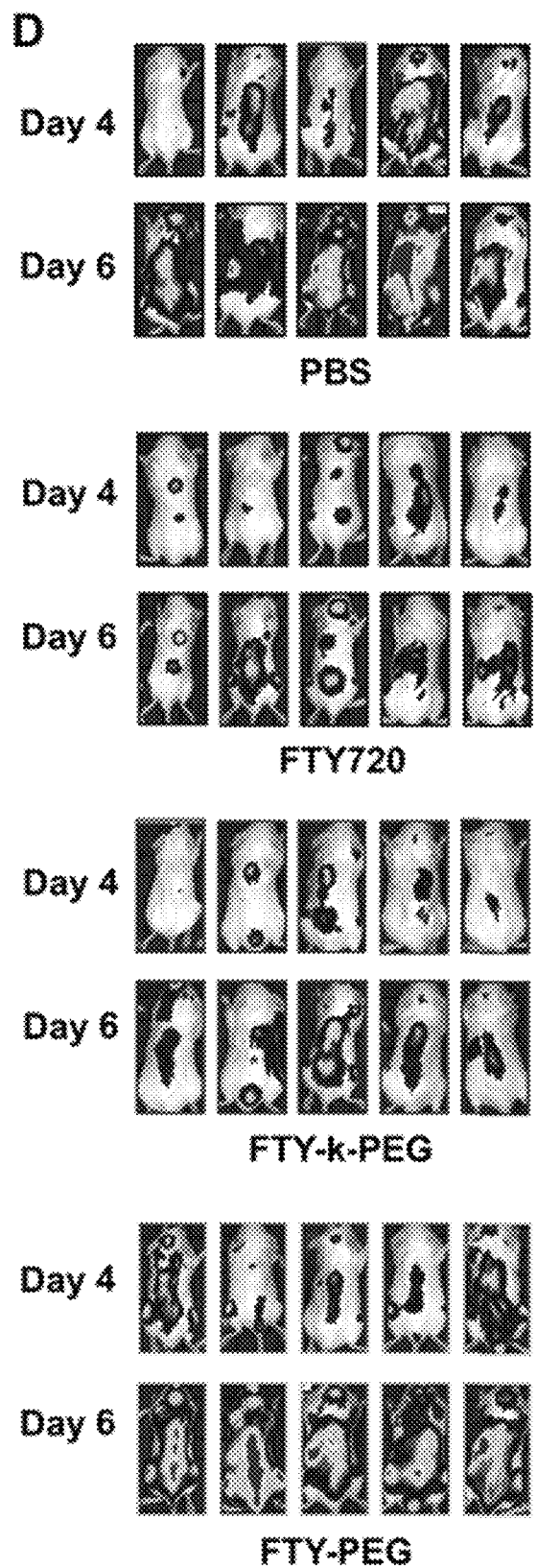

Preserved anti-leukemic effect of FTY-k-PEG in vivo. To assess the anti-leukemic effects of FTY-k-PEG in vivo while eliminating bradycardia and immunosuppressive activity, a BCR-Abl-driven leukemogenesis model in which fingolimod is effectively was used. Luciferase (Luc)-expressing, BCR-Abl p190-expressing FL5.12 (FL5.12/p190-Luc) cells were intravenously injected into Balb/c mice ($1 \times 10^5$ cells/mouse), and the mice were treated daily with i.p. injections of fingolimod, FTY-k-PEG, FTY-PEG (32 µmol/kg), or PBS over the course of 5 days after leukemia was established (see FIG. 12A). The leukemic expansion of FL5.12/p190-Luc cells was assessed by i.p. administration of synthetic firefly luciferin (120 mg/kg) and subsequent bioluminescence imaging (see FIG. 12B-D). There was a marked bioluminescence increase in mice treated with PBS and FTY-PEG indicating fast proliferation of BCR-Abl p190+ cells (see FIG. 12B, C). However, average bioluminescence signals in mice treated with fingolimod and FTY-k-PEG were 64% lower than that of PBS on day 6 (p<0.01). No significant difference was observed between fingolimod and FTY-k-PEG, confirming that FTY-k-PEG maintained the anti-leukemic properties of fingolimod without inducing bradycardia or lymphopenia (see FIG. 10). These results imply that the acid-transforming prodrug formulation is a viable option to utilize the therapeutic benefits of fingolimod against leukemia and other cancers with avoided adverse side effects. Since fingolimod is an FDA-approved drug for multiple sclerosis and is selectively toxic to cancerous cells, a viable prodrug formulation with a preserved anti-cancer activity with lowered toxicity is highly beneficial for fast clinical translation, not only for therapeutic efficacy but also improved quality of patient life post-treatment.

Figure 13A:
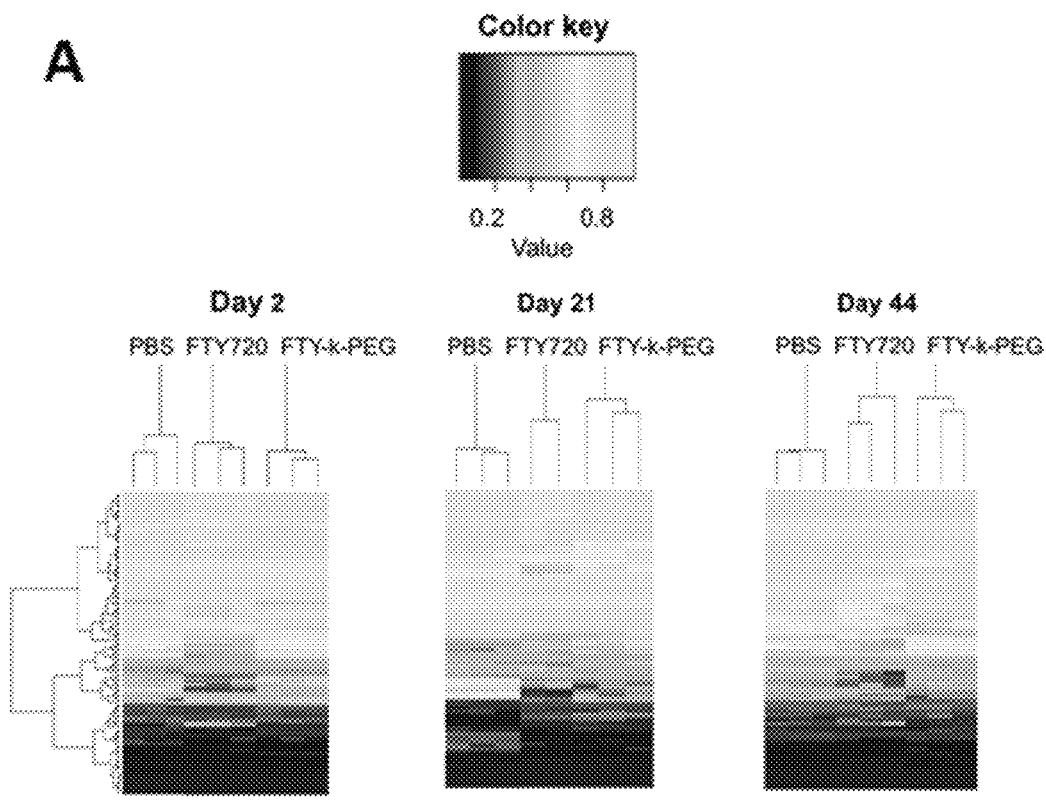
FIG. 13A-B demonstrates epigenetic biomarker differences between FTY and FTY-k-PEG. Healthy BALB/c mice were treated with fingolimod (10 mg/kg [32 μmol/kg]) or FTY-k-PEG (155 mg/kg [32 μmol/kg]) or PBS by daily i.p. injections for 14 days, and blood samples were taken 2 days post first treatment, 5 days after treatment ended, and 1 month after treatment. (A) Heatmap representation of differentially methylated regions used to calculate epigenetic age at various timepoints; (B) Epigenetic age generated from samples analyzed using proprietary markers for DNA methylation status. (n=3)
Figure 13B:
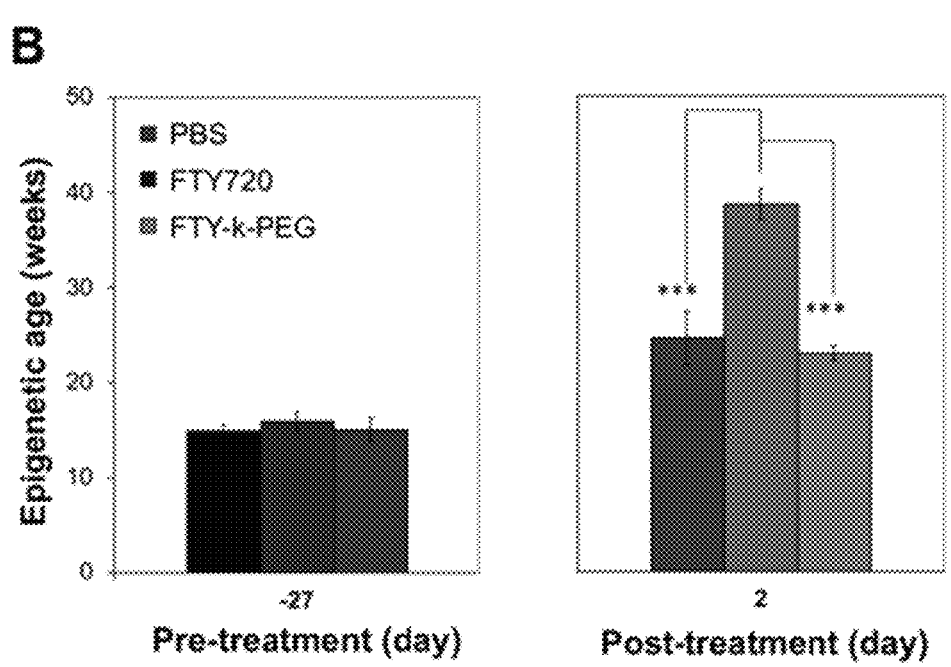
Figure 13B:
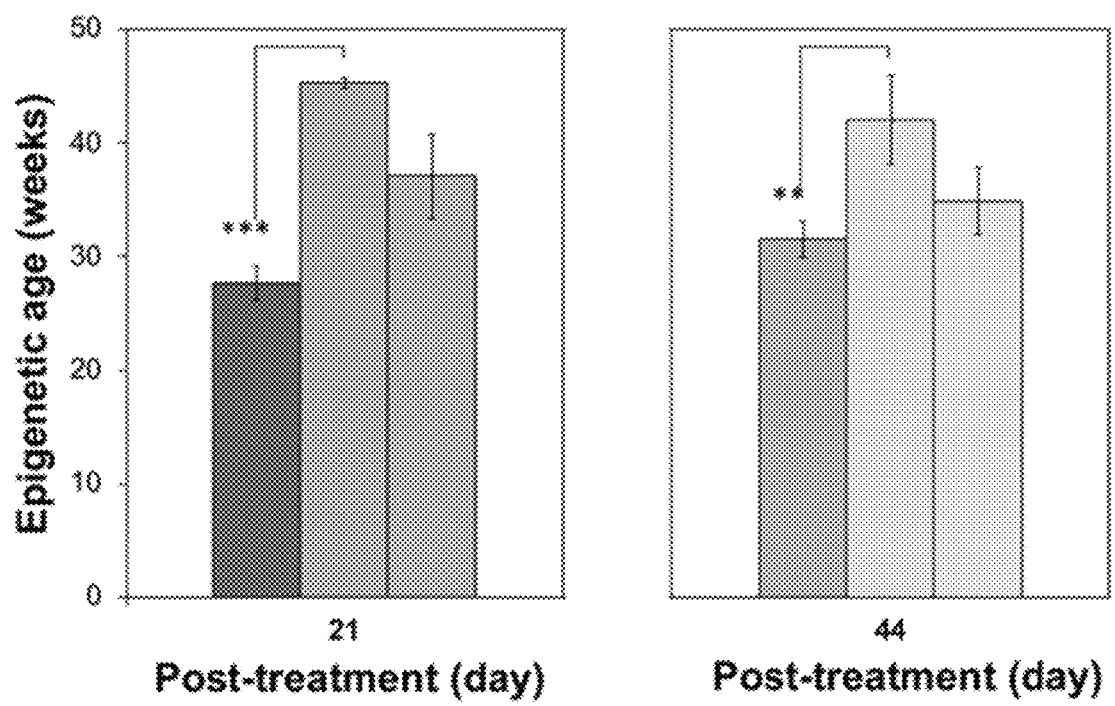

Minimized epigenetic age by FTY-k-PEG. DNA methylation-derived biomarkers are currently gaining significant interest as changes in epigenetic age is known to be associated with several pathological conditions including cancer as well as treatment with certain chemotherapeutic drugs. In attempts to explore epigenetic age as a possible means to quantitatively evaluate systemic toxicity of a drug, healthy female Balb/c mice were daily treated with i.p. injections of fingolimod, FTY-k-PEG, or PBS for two weeks, and blood samples were drawn prior to, during, and after treatment. Epigenetic age analysis was performed using Zymo Research Corporation's DNAge™ Epigenetic Aging Clock service, which assesses proprietary DNA methylation patterns known to specifically correlate epigenetic age to biological age. The methylated regions used for comparative analysis with corresponding methylation value (see FIG. 13A) showed clear differences in epigenetic biomarkers between FTY and FTY-k-PEG, and a significant increase in epigenetic age was observed in mice treated with fingolimod but not with FTY-k-PEG, two days post-treatment (see FIG. 13B). It was previously reported that bradycardia is most prevalent in the first 2 days after fingolimod administration, and it was within this timeframe when the greatest difference in epigenetic age was observed with FTY-k-PEG, possibly associated with avoided bradycardia and lymphopenia (see FIG. 10). Although further investigation into a likely correlation between fingolimod's toxicity and increased epigenetic age relative to control and FTY-k-PEG warrants further evaluation, epigenetic age analysis could be a promising way to quantitatively assess the adverse side effects of a drug at a molecular level, particularly on inflammation, disease development and progress, and other health issues.

Results Summary. The limited clinical use of fingolimod for cancer therapy due to bradycardia and lymphopenia was addressed by an fingolimod prodrug that remains inactive during circulation but converts into its active form upon exposure to mildly acidic intracellular conditions. The prodrug engineering utilized an acid-labile cyclic ketal group to conjugated PEG, resulting in FTY-k-PEG, in attempt to specifically inhibit phosphorylation of fingolimod that initiate the side effects. The synthetic methodology developed in this study is straightforward, scalable, and a less costly alternative to the development of an entirely new drug. FTY-k-PEG demonstrated nearly identical efficacy to free drug in BCR-Abl p190-driven leukemia model, both in vitro and in vivo, but without inducing bradycardia or lymphopenia. DNA methylation patterns known to be correlated with inflammation and disease implicated lower epigenetic damage by FTY-k-PEG. This study demonstrated that prodrug engineering to disrupt specific off-target molecular mechanisms can effectively improve safety profile of a drug.

It will be understood that various modifications may be made without departing from the spirit and scope of this disclosure. Accordingly, other embodiments are within the scope of the following claims.

What is claimed is:

1. A prodrug of fingolimod comprising an acid-labile linkage that when exposed to an environment that has a pH<7.0 releases the parent drug fingolimod, wherein the prodrug comprises the structure of Formula II:

Formula II

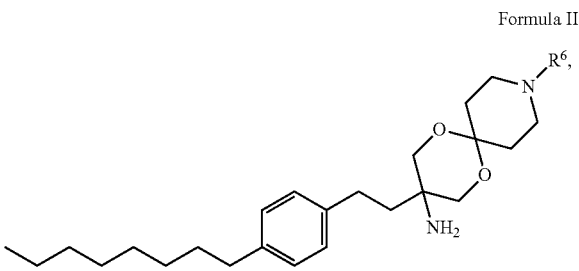

or a pharmaceutically acceptable salt or solvate thereof, wherein, $R^6$ is selected from H, D,

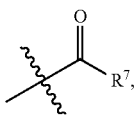

optionally substituted ($C_1$-$C_{30}$)alkyl, optionally substituted ($C_1$-$C_{30}$)heteroalkyl, optionally substituted ($C_1$-$C_{30}$)alkenyl, optionally substituted ($C_1$-$C_{30}$)heteroalkenyl, optionally substituted ($C_1$-$C_{30}$)alkynyl, optionally substituted ($C_1$-$C_{30}$)heteroalkynyl, optionally substituted aryl, optionally substituted ($C_3$-$C_{12}$)cycloalkyl, optionally substituted ($C_4$-$C_{12}$) cycloalkenyl, optionally substituted heterocycle, optionally substituted heteroaryl, optionally substituted mixed ring system, optionally substituted ($C_2$-$C_{30}$)-alkoxy, optionally substituted ($C_2$-$C_{30}$)-ester, polyethyleneimine, poly(glycolic acid), a poly(lactic acid), poly(glycolic-co-lactic acid), chitosan, poly(methacrylic acid), poly(acrylic acid), polycaprolactone, poly(ethylene/vinyl acetate), poly(vinyl acetate), poly(vinyl methyl ether), poly(vinyl alcohol), poly (N-isopropylacrylamide), —OH, a lipid, a saccharide, a polysaccharide, a nucleic acid, an amino acid, a peptide, a peptoid, a fatty acid, ethylene glycol, and polyethylene glycol; and $R^7$ is selected from an optionally substituted ($C_1$-$C_{30}$) alkyl, optionally substituted ($C_1$-$C_{30}$)heteroalkyl, optionally substituted ($C_1$-$C_{30}$)alkenyl, optionally substituted ($C_1$-$C_{30}$)heteroalkenyl, optionally substituted ($C_1$-$C_{30}$)alkynyl, optionally substituted ($C_1$-$C_{30}$)heteroalkynyl, optionally substituted aryl, optionally substituted ($C_3$-$C_{12}$)cycloalkyl, optionally substituted ($C_4$-$C_{12}$)cycloalkenyl, optionally substituted heterocycle, optionally substituted heteroaryl, optionally substituted mixed ring system, optionally substituted ($C_2$-$C_{30}$)-alkoxy, optionally substituted ($C_2$-$C_{30}$)-ester, polyethyleneimine, poly(glycolic acid), a poly(lactic acid), poly(glycolic-co-lactic acid), chitosan, poly(methacrylic acid), poly(acrylic acid), polycaprolactone, poly(ethylene/vinyl acetate), poly(vinyl acetate), poly(vinyl methyl ether), poly(vinyl alcohol), poly (N-isopropylacrylamide), —OH, a lipid, a saccharide, a polysaccharide, a nucleic acid, an amino acid, a peptide, a peptoid, a fatty acid, ethylene glycol, and polyethylene glycol.

2. The prodrug of claim 1, wherein the prodrug does not readily release the parent drug when exposed to physiological pH of 7.4.

3. The prodrug of claim 1, wherein the parent drug is readily released from the prodrug when exposed to a pH from 4.2 to 6.7.

4. The prodrug of claim 1, wherein the prodrug in comparison to the parent drug is protected/shielded from phosphorylation during circulation in vivo or prior to endocytosis.

5. The prodrug of claim 1, wherein the prodrug is a pharmaceutically acceptable salt form of the prodrug having the structure of Formula II(a):

Formula II(a)

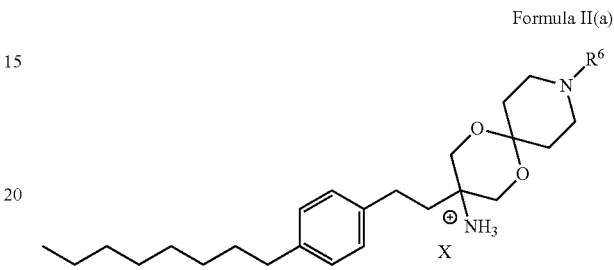

wherein, $R^6$ is selected from H, D,

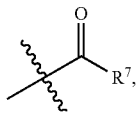

optionally substituted ($C_1$-$C_{30}$)alkyl, optionally substituted ($C_1$-$C_{30}$)heteroalkyl, optionally substituted ($C_1$-$C_{30}$)alkenyl, optionally substituted ($C_1$-$C_{30}$)heteroalkenyl, optionally substituted ($C_1$-$C_{30}$)alkynyl, optionally substituted ($C_1$-$C_{30}$)heteroalkynyl, optionally substituted aryl, optionally substituted ($C_3$-$C_{12}$)cycloalkyl, optionally substituted ($C_4$-$C_{12}$) cycloalkenyl, optionally substituted heterocycle, optionally substituted heteroaryl, optionally substituted mixed ring system, optionally substituted ($C_2$-$C_{30}$)-alkoxy, optionally substituted ($C_2$-$C_{30}$)-ester, polyethyleneimine, poly(glycolic acid), a poly(lactic acid), poly(glycolic-co-lactic acid), chitosan, poly(methacrylic acid), poly(acrylic acid), polycaprolactone, poly(ethylene/vinyl acetate), poly(vinyl acetate), poly(vinyl methyl ether), poly(vinyl alcohol), poly (N-isopropylacrylamide), —OH, a lipid, a saccharide, a polysaccharide, a nucleic acid, an amino acid, a peptide, a peptoid, a fatty acid, ethylene glycol, and polyethylene glycol;

$R^7$ is selected from optionally substituted ($C_1$-$C_{30}$) alkyl, optionally substituted ($C_1$-$C_{30}$)heteroalkyl, optionally substituted ($C_1$-$C_{30}$)alkenyl, optionally substituted ($C_1$-$C_{30}$)heteroalkenyl, optionally substituted ($C_1$-$C_{30}$)alkynyl, optionally substituted ($C_1$-$C_{30}$)heteroalkynyl, optionally substituted aryl, optionally substituted ($C_3$-$C_{12}$)cycloalkyl, optionally substituted ($C_4$-$C_{12}$)cycloalkenyl, optionally substituted heterocycle, optionally substituted heteroaryl, optionally substituted mixed ring system, optionally substituted ($C_2$-$C_{30}$)-alkoxy, optionally substituted ($C_2$-$C_{30}$)-ester, polyethyleneimine, poly(glycolic acid), a poly(lactic acid), poly(glycolic-co-lactic acid), chitosan, poly(methacrylic acid), poly(acrylic acid), polycaprolactone, poly(ethylene/vinyl acetate), poly(vinyl acetate), poly(vinyl methyl ether), poly(vinyl alcohol), poly (N-isopropylacrylamide), —OH, a lipid, a saccharide, a polysaccharide, a nucleic acid, an amino acid, a peptide, a peptoid, a fatty acid, ethylene glycol, and polyethylene glycol; and X is a counterion selected from the group consisting of acetate, aspartate, benzenesulfonate, benzoate, besylate, bicarbonate, bitartrate, bromide, camsylate, carbonate, chloride, citrate, decanoate, edetate, esylate, fumarate, gluceptate, gluconate, glutamate, glycolate, hexanoate, hydroxynaphthoate, iodide, isethionate, lactate, lactobionate, malate, maleate, mandelate, mesylate, methylsulfate, mucate, napsylate, nitrate, octanoate, oleate, pamoate, pantothenate, phosphate, polygalacturonate, propionate, salicylate, stearate, succinate, sulfate, tartrate, teoclate and tosylate.

6. The prodrug of claim 1, wherein the prodrug comprises the structure of Formula III:

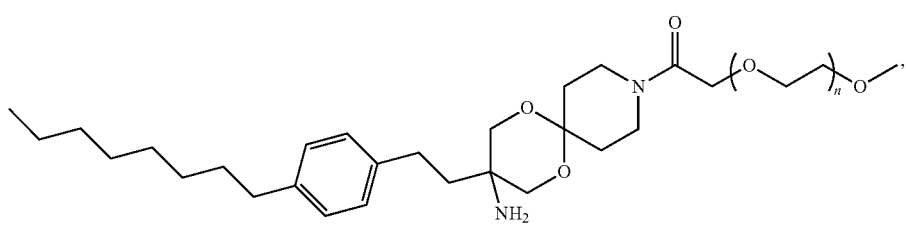

Formula III or a pharmaceutically acceptable salt or solvate thereof, wherein, n is an integer selected from 1 to 400,000.

7. The prodrug of claim 6, wherein the prodrug is a pharmaceutically acceptable salt form of the prodrug having the structure of Formula III(a):

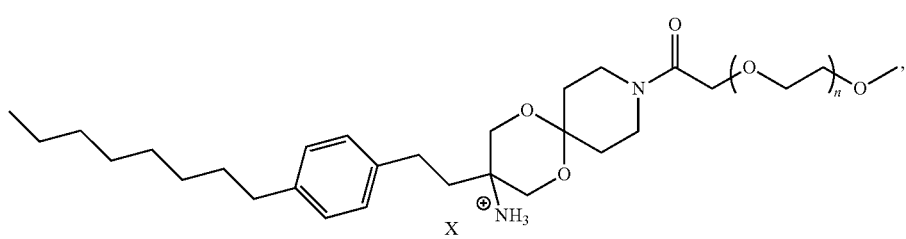

Formula III(a)

wherein, n is an integer selected from 1 to 400,000,

X is a counterion selected from the group consisting of acetate, aspartate, benzenesulfonate, benzoate, besylate, bicarbonate, bitartrate, bromide, camsylate, carbonate, chloride, citrate, decanoate, edetate, esylate, fumarate, gluceptate, gluconate, glutamate, glycolate, hexanoate, hydroxynaphthoate, iodide, isethionate, lactate, lactobionate, malate, maleate, mandelate, mesylate, methylsulfate, mucate, napsylate, nitrate, octanoate, oleate, pamoate, pantothenate, phosphate, polygalacturonate, propionate, salicylate, stearate, succinate, sulfate, tartrate, teoclate and tosylate.

8. A pharmaceutical composition comprising the prodrug of claim 1 and a pharmaceutically acceptable carrier, diluent, and/or excipient.

9. The pharmaceutical composition of claim 8, wherein the pharmaceutical composition is formulated for parenteral administration.

10. The pharmaceutical composition of claim 8, wherein the pharmaceutical composition is formulated for oral administration in the form of enterically coated tablets or capsules.

11. A method of treating a subject with a cancer, comprising:

administering a therapeutically effective amount of the prodrug of claim 1 to the subject in need of treatment thereof.

12. The method of claim 11, wherein the cancer is selected from chronic myelogenous leukemia (CML), acute lymphoblastic leukemia (ALL), non-small cell lung cancer (NSCLC), breast cancer, melanoma, colorectal cancer, and ovarian cancer.

13. The method of claim 11, wherein the prodrug is administered at a dose from 100 mg/kg to 500 mg/kg.

14. The method of claim 11, wherein the prodrug is administered sequentially or concurrently with one or more anticancer therapeutic agents selected from the group consisting of angiogenesis inhibitors, tyrosine kinase inhibitors, PARP inhibitors, alkylating agents, vinca alkaloids, anthracyclines, antitumor antibiotics, antimetabolites, topoisomerase inhibitors, aromatase inhibitors, mTor inhibitors, retinoids, and HDAC inhibitors.

15. A method of treating a subject with multiple sclerosis, comprising:

administering an effective amount of the prodrug of claim 1 to the subject in need of treatment thereof.

16. The method of claim 15, wherein the prodrug is administered sequentially or concurrently with one or more multiple sclerosis treatments selected from the group consisting of beta interferons, glatiramer acetate, dimethyl fumarate, teriflunomide, siponimod, ocrelizumab, natalizumab, alemtuzumab, and mitoxantrone.

* * * * *